(12) United States Patent
Wong et al.

(10) Patent No.: US 7,906,136 B2
(45) Date of Patent: Mar. 15, 2011

(54) CONVENIENTLY IMPLANTABLE SUSTAINED RELEASE DRUG COMPOSITIONS

(75) Inventors: Vernon G. Wong, Menlo Park, CA (US); Louis L. Wood, Potomac, MD (US)

(73) Assignee: Ramscor, Inc., Menlo Park, CA (US)

(*) Notice: Subject to any disclaimer, the term of this patent is extended or adjusted under 35 U.S.C. 154(b) by 490 days.

(21) Appl. No.: 11/236,426

(22) Filed: Sep. 27, 2005

(65) Prior Publication Data
US 2006/0073182 A1 Apr. 6, 2006

Related U.S. Application Data

(60) Provisional application No. 60/614,484, filed on Oct. 1, 2004, provisional application No. 60/709,665, filed on Aug. 19, 2005.

(51) Int. Cl.
*A61F 2/00* (2006.01)
(52) U.S. Cl. ........................................................ 424/428
(58) Field of Classification Search .................. 424/426, 424/427
See application file for complete search history.

(56) References Cited

U.S. PATENT DOCUMENTS

| | | | |
|---|---|---|---|
| 4,096,271 A * | 6/1978 | De Lis Masilungan | 514/368 |
| 4,304,765 A * | 12/1981 | Shell et al. | 424/427 |
| 4,309,996 A * | 1/1982 | Theeuwes | 604/892.1 |
| 4,568,547 A | 2/1986 | Herschler | |
| 4,728,721 A | 3/1988 | Yamamoto et al. | |
| 4,853,224 A | 8/1989 | Wong | |
| 4,997,652 A | 3/1991 | Wong | |
| 5,164,188 A | 11/1992 | Wong | |
| 5,371,078 A * | 12/1994 | Clark et al. | 514/182 |
| 5,443,505 A | 8/1995 | Wong et al. | |
| 5,620,700 A * | 4/1997 | Berggren et al. | 424/435 |
| 5,632,984 A | 5/1997 | Wong et al. | |
| 5,653,992 A | 8/1997 | Bezwada et al. | |
| 5,766,242 A | 6/1998 | Wong et al. | |
| 5,770,589 A | 6/1998 | Billson et al. | |
| 5,824,072 A | 10/1998 | Wong | |
| 5,869,079 A | 2/1999 | Wong et al. | |
| 5,945,115 A | 8/1999 | Dunn et al. | |
| 6,130,200 A | 10/2000 | Brodbeck et al. | |
| 6,174,540 B1 | 1/2001 | Williams et al. | |
| 6,214,838 B1 | 4/2001 | Sohda et al. | |
| 6,331,311 B1 | 12/2001 | Brodbeck et al. | |
| 6,331,313 B1 | 12/2001 | Wong et al. | |
| 6,369,116 B1 | 4/2002 | Wong et al. | |
| 6,468,961 B1 | 10/2002 | Brodbeck et al. | |
| 6,537,566 B1 | 3/2003 | Copland et al. | |
| 6,653,288 B1 | 11/2003 | Beuvry et al. | |
| 6,699,493 B2 | 3/2004 | Wong | |
| 6,726,918 B1 | 4/2004 | Wong et al. | |
| 6,733,786 B1 * | 5/2004 | Kim et al. | 424/486 |
| 6,827,931 B1 | 12/2004 | Donovan | |
| 6,855,340 B2 | 2/2005 | Brewer | |
| 7,074,426 B2 | 7/2006 | Kochinke | |
| 2002/0064547 A1 | 5/2002 | Chem et al. | |
| 2003/0044467 A1 | 3/2003 | Brodbeck et al. | |
| 2003/0211123 A1 * | 11/2003 | Shukla et al. | 424/400 |
| 2003/0216303 A1 * | 11/2003 | Ambuhl et al. | 514/11 |
| 2004/0092435 A1 | 5/2004 | Peyman | |
| 2004/0106914 A1 * | 6/2004 | Coppeta et al. | 604/892.1 |
| 2004/0151753 A1 | 8/2004 | Chen et al. | |
| 2004/0151754 A1 | 8/2004 | Ashton | |
| 2005/0101517 A1 * | 5/2005 | De Nijs et al. | 514/1 |
| 2005/0118206 A1 * | 6/2005 | Luk et al. | 424/400 |
| 2005/0143363 A1 * | 6/2005 | De Juan et al. | 514/179 |
| 2005/0244469 A1 * | 11/2005 | Whitcup et al. | 424/427 |

FOREIGN PATENT DOCUMENTS

| | | | |
|---|---|---|---|
| CA | 2 436 361 A1 * | 8/2002 | |
| WO | WO 00/71163 A1 | 11/2000 | |
| WO | WO 01/70256 A1 | 9/2001 | |
| WO | WO 2004/011054 A2 | 2/2004 | |
| WO | WO 2004/081196 A2 | 9/2004 | |

OTHER PUBLICATIONS

Coleman et al., 37(12) J. Pharm. Pharmacol. 878-83 (1985).
Fishman et al., 27(7) Invest. Ophthalmol. Vis. Sci. 1103-06 (1986).
Migally, 2(4) Arch. Androl. 365-69 (1979).
Wang et al., 90 J. Cont. Release 345-54 (2003).
Supplementary European Search Report dated Aug. 13, 2009.

* cited by examiner

*Primary Examiner* — Robert A Wax
*Assistant Examiner* — Bethany Barham
(74) *Attorney, Agent, or Firm* — Mary S. Webster; Nixon Peabody, LLP

(57) ABSTRACT

This invention provides for biocompatible and biodegradable syringeable liquid, implantable solid, and injectable gel pharmaceutical formulations useful for the treatment of systemic and local disease states.

9 Claims, 12 Drawing Sheets

CONVENIENTLY IMPLANTABLE SUSTAINED RELEASE DRUG COMPOSITIONS

CROSS REFERENCE TO RELATED APPLICATIONS

This application claims the benefit under 35 U.S.C. §119 (e) of U.S. provisional patent application Ser. No. 60/614,484, filed on Oct. 1, 2004, by Vernon G. Wong and Louis L. Wood, entitled Conveniently Implantable Sustained Release Drug Compositions, and U.S. provisional patent application Ser. No. 60/709,665, filed on Aug. 19, 2005, by Vernon G. Wong and Louis L. Wood entitled Conveniently Implantable Sustained Release Drug Compositions, both of which are incorporated herein by reference in their entirety.

FIELD OF THE INVENTION

This invention provides for biocompatible and biodegradable syringeable liquid, implantable solid, and injectable gel pharmaceutical formulations useful for the treatment of systemic and local diseases.

BACKGROUND OF THE INVENTION

Present modes of drug delivery such as topical application, oral delivery, and intramuscular, intravenous and subcutaneous injection may result in high and low blood concentrations and/or shortened half-life in the blood. In some cases, achieving therapeutic efficacy with these standard administrations requires large doses of medications that may result in toxic side effects. The technologies relating to controlled drug release have been attempted in an effort to circumvent some of the pitfalls of conventional therapy. Their aims are to deliver medications on a continuous and sustained manner. Additionally, local control drug release applications are site or organ specific.

In response to these issues, reservoir delivery systems have been explored. Non-biodegradable drug delivery systems include, for example, Vitrasert® (Bausch & Lomb), a surgical implant that delivers ganciclovir intraocularly; Duros® (Durect Corp.), surgically implanted osmotic pump that delivers leuprolide actetate to treat advanced prostate cancer; and Implanon® (Organon International), a type of subdermal contraceptive implant.

Biodegradable implants include, for example, Lupron Depot (TAP Pharmaceutical Prods., Inc.), a sustained-release microcapsule injection of luteinizing hormone-releasing hormone (LH-RH) analog for the treatment of prostate cancer; the Surodex® dexamethasone anterior segment drug delivery system (Oculex Pharmaceuticals, Inc.), and Nutropin Depto® (Genentech), micronized particles of recombinant human growth hormone embedded in polylactide-coglycolide (PLG) microspheres.

Additionally, polyethylene glycol conjugations (pegylation) to reduce the frequency of administration are now in use. One example, pending FDA licensure, is Macugen™ (Eyetech Pharmaceuticals, Inc.), a pegylated anti-VEGF aptamer, for use in treating wet macular degeneration.

There remains a need for a more economical, practical, and efficient way of producing and manufacturing drug delivery systems that could be used locally or systemically, in solid, semi-solid, or liquid formulations.

SUMMARY OF THE INVENTION

An object of the present invention provides for economical, practical, and efficient drug delivery system. According to the present invention, this drug delivery system is produced easily, delivered easily to the site of indication, and is both biocompatible and biodegradable. More specifically, the formulations of the present invention provide for novel therapies that are easily manipulated and injected or implanted by qualified medical practitioners. The formulations deliver therapeutic and non-toxic levels of active agents over the desired extended time frame, primarily at the site of implantation. The formulations are both biocompatible and biodegradable, and disappear harmlessly after delivering active agent to the desired site.

One embodiment of the present invention provides for a pharmaceutical formulation for implantation into a patient for the sustained release of an active agent comprising a biocompatible, biodegradable excipient and an active agent or pharmaceutically acceptable salt thereof. In an aspect of the invention, the formulation is capable of being implanted by injection.

Another embodiment of the invention provides for a pharmaceutical formulation for implantation into a patient for the sustained release of an active agent comprising a biocompatible, biodegradable excipient and an active agent or pharmaceutically acceptable salt thereof, wherein said formulation exhibits an in vitro dissolution profile wherein about 2% to about 100% of the active agent is released over a period ranging from about 1 day to at least 365 days.

Yet another embodiment provides for a pharmaceutical formulation for implantation into a patient for the sustained release of an active agent comprising a biocompatible, biodegradable excipient and an active agent or pharmaceutically acceptable salt thereof, wherein about 2% to about 60% of the active agent is released over a period ranging from about 1 day to about 105 days. Alternatively, about 2% to about 100% of the active agent may be released over a period of about 25 days. Or about 2% to about 85% of the active agent may be released over a period of about 30 days to about 60 days. In another embodiment, about 2% to about 60% of the active agent is released over a period ranging from about 80 days to about 100 days.

In another aspect of the invention, the formulation comprises an active agent at a concentration from about 5% to about 50% of the implant and includes a biodegradable, biocompatible excipient at a concentration of at least about 5% percent of the implant.

In another embodiment, the biocompatible, biodegradable excipient may be tocopherol isomers and/or their esters; tocotrienols and/or their esters; benzyl alcohol; benzyl benzoate; those dibenzoate esters of poly(oxyethylene) diols having low water solubility; dimethyl sulfone; poly(oxypropylene) diols having low water solubility; the mono, di, and triesters of O-acetylcitric acid with $C_1$-$C_{10}$ straight and branched chain aliphatic alcohols; and liquid and semisolid polycarbonate oligomers.

An aspect of the invention provides for a controlled and sustained drug delivery system for the posterior segment of the eye, comprised of a biodegradable and biocompatible liquid matrix for direct injection. In particular, this aspect of the invention provides for a composition comprising dexamethasone or triamcinolone acetonide and benzyl benzoate. In an aspect of this embodiment, dexamethasone or triamcinolone acetonide is released into the vitreous of the eye in an amount ranging from about 20 µg/ml to less than about 1.0 µg/ml over a period of about sixty to about ninety days.

The active agent envisioned in an embodiment of the present invention is selected from the group consisting of analgesics, anesthetics, narcotics, angiostatic steroids, anti-inflammatory steroids, angiogenesis inhibitors, nonsteroidal anti-inflammatories, anti-infective agents, anti-fungals, anti-malarials, anti-tublerculosis agents, anti-virals, alpha androgenergic agonists, beta adrenergic blocking agents, carbonic anhydrase inhibitors, mast cell stabilizers, miotics, prostaglandins, antihistamines, antimicrotubule agents, antineoplastic agents, antipoptotics, aldose reductase inhibitors, antihypertensives, antioxidants, growth hormone agonists and antagonists, vitrectomy agents, adenosine receptor antagonists, adenosine deaminase inhibitor, glycosylation antagonists, anti aging peptides, topoisemerase inhibitors, anti-metabolites, alkylating agents, antiandrigens, anti-oestogens, oncogene activation inhibitors, telomerase inhibitors, antibodies or portions thereof, antisense oligonucleotides, fusion proteins, luteinizing hormone releasing hormones agonists, gonadotropin releasing hormone agonists, tyrosine kinase inhibitors, epidermal growth factor inhibitors, ribonucleotide reductase inhibitors, cytotoxins, IL2 therapeutics, neurotensin antagonists, peripheral sigma ligands, endothelin ETA/receptor antagonists, antihyperglycemics, anti-glaucoma agents, anti-chromatin modifying enzymes, insulins, glucagon-like-peptides, obesity management agents, anemia therapeutics, emesis therapeutics, neutropaenia therapeutics, tumor-induced hypercalcaemia therapeutics, blood anticoagulants, immunosuppressive agents, tissue repair agents, psychotherapeutic agents, botulinum toxins (Botox, Allergan), and nucleic acids such as siRNA and RNAi.

DETAILED DESCRIPTION OF THE INVENTION

Figure 1:
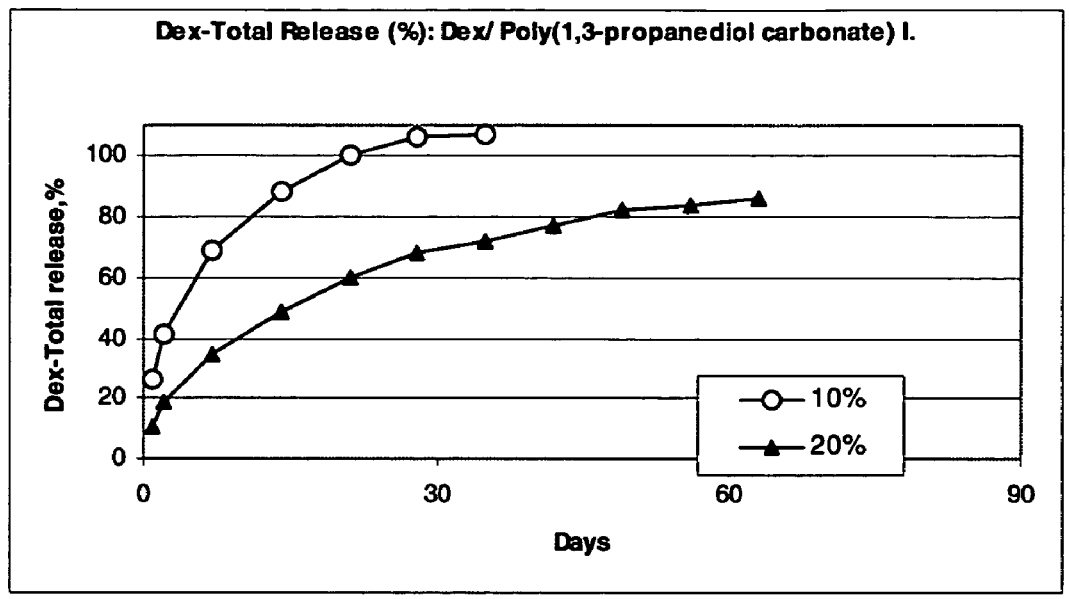
FIG. 1 presents dissolution profiles of dexamethasone (Dex) from two formulations of Dex/poly(1,3-propanediol carbonate)I.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to an excipient is a reference to one or more such excipients, including equivalents thereof known to those skilled in the art. Other than in the operating examples, or where otherwise indicated, all numbers expressing quantities of ingredients or reaction conditions used herein should be understood as modified in all instances by the term "about." The term "about" when used in connection with percentages may mean ±1%.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. This application is related to U.S. provisional patent application Ser. No. 60/614,484, filed on Oct. 1, 2004, by Vernon G. Wong and Louis L. Wood, entitled Conveniently Implantable Sustained Release Drug Compositions, and U.S. provisional patent application Ser. No. 60/709,665, filed on Aug. 19, 2005, by Vernon G. Wong and Louis L. Wood entitled Conveniently Implantable Sustained Release Drug Compositions, both of which are incorporated herein by reference in their entirety.

Unless defined otherwise, all technical and scientific terms used herein have the same meaning as those commonly understood to one of ordinary skill in the art to which this invention pertains.

The present invention relates to novel biocompatible, biodegradable sustained release formulations. In one aspect of the invention, these formulations are syringeable liquids, mechanically cohesive solids, injectable gels, or emulsified m/cells (oil in water or water in oil). A desirable feature of these liquid, solid, and gel formulations is that they maintain a single bolus or pellet shape at the site of their placement. That is, they do not break up as a multitude of smaller droplets or particles that migrate away from their intended point of placement and/or by virtue of a resultant increase in surface area greatly alter the intended release rate of their drug content.

The formulations of the present invention provide for novel therapies that are easily manipulated and injected or implanted by qualified medical practitioners. The formulations deliver therapeutic and non-toxic levels of active agents over the desired extended time frame, primarily at the site of implantation. The formulations are both biocompatible and biodegradable, and disappear harmlessly after delivering active agent to the desired site.

The present invention relates generally, but not totally, to the use of formulations that are of limited solubility, biocompatible, and biodegradable (LSBB), which may also be syringeable, for controlled and sustained release of an active agent or a combination of active agents. Solid, gel, or injectable controlled-sustained release systems can be fabricated by combining LSBB and an active agent. Systems can combine more than one biodegradable component as well as more than one active agent. Solid forms for implantation can be produced by tableting, injection molding or by extrusion. Gels can be produced by vortex or mechanical mixing. Injectable formulations can be made by pre-mixing in a syringe or mixing of the LSBB and the active agent before or at the time of administration. Formulations may serve as coating for stents or other implants by, for example, dipping the stent in a liquid form of the formulation and then drying it.

In an aspect of the present invention, novel biocompatible and biodegradable syringeable liquid, implantable cohesive solids, and injectable gel formulations conveniently placed on or within the human or animal body for the sustained release of active agents, are obtained by admixing one or more excipients, such as, for example: benzyl alcohol; benzyl benzoate; diethylene glycol dibenzoate; triethylene glycol dibenzoate; dibenzoate esters of poly(oxyethylene) diols up to about 400 mwt; propylene glycol dibenzoate; dipropylene glycol dibenzoate; tripropylene glycol dibenzoate; dibenzoate esters of poly(oxypropylene) diols up to about 3000 mwt; poly(oxypropylene) diols up to about 3000 mwt; dimethyl sulfone; the various isomers of tocopherol; tocopherol acetate and tocopherol succinate, tocotrienol isomers and their esters, perfluorohexane, polymeric polycarbonate oligomers, and the mono, di, and triesters of O-acetylcitric acid with $C_1$-$C_{10}$ straight and branched chain aliphatic alcohols, with a large number of established and new active agents.

In another aspect of the invention, the solid form generally contains about 1% to about 60% of an LSBB, the gel form generally contains about 20% to about 80% of an LSBB, and an injectable form (which may be a gel or liquid form) generally contains about 30% to about 99.9% of an LSBB.

Liquid and Solid LSBBs can be implanted, for example, surgically, by trocar, or by needle introduction. It can be placed into body cavities such as joints by methods well-known in the art (typically using the procedures outlined by Cardone & Tallia, Am. Family Physician, 66(2), 283-92 (2002); 66(11), 2097-100 (2002); 67(10), 2147-52 (2003); 68(7), 1356-62 (2003); 67(4), 745-50 (2003)); intraocular (chambers such as the anterior chamber and posterior segment of the eye); intratumoral injection into the prostate tumor (typically using a procedure similar to that described by Jackson et al., 60(5) Cancer Res., 4146-51 (2000)); intratumoral injection into inoperable tumors (such as gliomas) in the brain (typically using a procedure similar to that described by Emerich et al., 17(7) Pharm Res, 767-75 (2000)); injection or insertion into an intravertebral disc or disc space; injection into peritoneal cavity or, intranasal, intrathecal, subcutaneous, or intramuscular injection, injection into the epidural, subdural and/or subarachnoid space; or it can be injected or inserted directly into the cerebral spinal fluid through the spinal canal or into the CNS ventricular system.

Additionally, for localized active agent delivery, the system of the present invention may be surgically implanted at or near the site of action. This may be useful when it is used, for example, in treating ocular conditions, primary tumors, rheumatic and arthritic conditions, and chronic pain.

It is contemplated that these LSBB/active agent compositions can be applied to the following, but not limited to, systems of the human or animal body: muscular, skeletal, nervous, autonomic nervous, vascular, lymphatic, digestive, respiratory, urinary, female reproductive, male reproductive, endocrine or intraparenchymal, to provide a wide variety of sustained therapies.

Specific areas of the human or animal body to be targeted for injection or implantation or topical applications of these LSBB/active agents compositions include, but are not limited to: heart, brain, spinal nerves, vertebral column, skull, neck, head, eye, ear organs of hearing and balance, nose, throat, skin, viscara, hair, shoulder, elbow, hand, wrist, hip, knee, ankle, foot, teeth, gums, liver, kidney, pancreas, prostate, testicles, ovaries, thymus, adrenal glands, pharynx, larynx, bones, bone marrow, stomach, bowel, upper and lower intestines, bladder, lungs, mammaries. Surgical mplantation into the eye, for example, is known in the art as described in U.S. Pat. Nos. 6,699,493; 6,726,918; 6,331,313; 5,824,072; 5,766, 242; 5,443,505; 5,164,188; 4,997,652; and 4,853,224.

Solid LSBB, for example, may be implanted directly into parenchymal tissues such as the brain, spinal cord, or any part of the CNS system, into the kidney, liver, spleen, pancreas, lymph nodes as well as tumors. Gel LSBB systems may be applied to surface tissues such as the skin, or as coating on surfaces of parenchymal organs to be absorbed, or be applied directly on the cornea, conjunctiva and on the sclera for delivery of active agent onto the surface and intraocularly of the eye. Injectable LSBB is less invasive and can be delivered, for example, through a 30 gauge needle into the eye, or through larger needles into cavities like joints.

The system according to the present invention has particular applicability in providing a controlled and sustained release of active agents effective in obtaining a desired local or systemic physiological or pharmacological effect relating at least to the following areas: treatment of cancerous primary tumors, chronic pain, arthritis, rheumatic conditions, hormonal deficiencies such as diabetes and dwarfism, modification of the immune response such as in the prevention and treatment of transplant rejection and in cancer therapy. The system is also suitable for use in treating HIV and HIV related opportunistic infections such as CMV, toxoplasmosis, *pneumocystis carinii* and *mycobacterium avium* intercellular. The system may be used to delivery an active agent effective in treating fungal infection of the mouth. If such a use is desired, the system may be designed to have a shape suitable for implanting into a tooth.

LSBB is also useful for treating ocular conditions such as glaucoma, PVR, diabetic retinopathy, uveitis, retinal edema, vein occulusion, macular degeneration, Irvine-Gass Syndrome and CMV retinitis, corneal diseases such as keratitis and corneal transplantation and rejection. The formulations may also be prepared as control release eye drops for dry-eye or for controlling the immune response. Regarding control of immune responses, the formulations may contain cyclosporine, sirolimus, or tacrolimus. Other intraocular uses include glaucoma treatments (formulations including timolol), antibiotic delivery, antiproliferatives delivery (e.g., paclitaxel).

Other uses of the formulations include, for example, mediating homograft rejection with formulations comprising surolimus or cyclosporine. Local cancer therapy may be delivered to, for example, the kidney or liver, using in formulations comprising, for example, adriamycin or small epidermal growth factors. Prostate cancer may be treated with formulations including fenasteride. Cardiac stents implants, central nervous system implants (e.g., spinal implants), orthopedic implants, etc., may be coated with formulations including growth or differentiation factors, anti-inflammatory agents, or antibiotics.

The technology of the present application is useful in overcoming the difficulties reported in some cases of achieving therapeutic efficacy, as experienced in current administrations requiring large doses of medications that may result in toxic side effects. An important example of this problem is the current clinical practice of intravitreal injections of microcrystalline triamcinolone acetonide (TA) for the treatment of intraocular neovascular, oedematous, or inflammatory diseases. See Jonas et al., 24(5) Prog Retin Eye Res. 587-611 (2005), and references therein. The therapy requires the presence of a solution of the proper TA concentration in the vitreous chamber for periods of six months to a year and possibly longer. The therapeutic vitreal concentrations of TA seem to be at 1.0 $\mu$g/ml or below (Matsuda et al., 46 Invest Ophthalmol Vis Sci. 1062-1068 (2005)) whereas harmful complications (glaucoma, cataracts, cytotoxicity) can arise when TA concentrations continuously exceed 10 $\mu$g/ml over an extended period of time. See Gillies et al., 122(3) Arch Ophthalmol. 336-340 (2004); Jonas et al., 15(4) Eur J Ophthalmol. 4624 (2005); Yeung et al, 44 Invest Ophthalmol Vis Sci. 5293-5300 (2003). The desire to limit TA administration to one or two injections per year (obvious patient comfort coupled with the possibility of endophthalmitis (see Bucher et al., 123(5) Arch Ophthalmol. 649-53 (2005)), conflicts with the ability of supplying enough TA crystals without excursions into toxic concentrations. The novel compositions of this invention solve this problem by encompassing the desired amounts of TA crystals in an injectable, biocompatible, bioerodable medium that continuously regulates the release of safe, therapeutic levels of intravitreal TA for periods of six months or more.

Further regarding ocular conditions, metabolic and inflammation conditions in the posterior segment of the eye have been extremely difficult to treat. Such conditions as proliferative vitreoretinopathy (PVR), uveitis, cystoid macular edema (CME), diabetes, and macular degeneration are major causes of blindness. Conventional methods of drug delivery, including topical, periocular, subconjunctival or systemic administration, have had limited success due in large part to poor drug penetration (due to the blood-eye barrier) and toxic side effects. One efficient way of delivering a drug to the posterior segment is to place it directly into the vitreous cavity. Intravitreal drug injections have shown promising results in animals and in humans, but repeated and frequent injections have had to be performed to maintain therapeutic levels.

For example, direct injection of corticosteroids, particularly triamcinolone acetonide, has been effective particularly in selected wet AMD and in diabetic retinal edemas. Because of the drug's short half-life in the eye, frequent injections are required. Moreover, because the drug is being given in a bolus, uncontrolled high and then low drug concentration levels are encountered. As a consequence, adverse reactions such as infection, glaucoma, cataract formation, retinal detachment and intraocular bleeding have been common adverse occurrences. Vitrasert® (Bausch & Lomb) is a six to eight month reservoir system to treat CMV retinitis with the antiviral gancyclovir. This is a non-biodegradable system and must be both inserted and removed surgically. Similarly, Posurdex® (Allergan Pharma) is a one-month biodegradable delivery system that must be implanted surgically into the eye, and contains dexamethasone and PLGA for the treatment of posterior segment pathologies.

Hence, one embodiment of the present invention provides for an intraocular controlled and sustained drug delivery system for the posterior segment of the eye. It is comprised of a biodegradable and biocompatible liquid matrix containing a microdispersed drug or mixture of drugs, and can be injected directly into the posterior segment with a relatively small needle. The duration of drug delivery can be as short as a few days to many months and up to one year or longer, and the matrix gradually and safely dissipates over time so that there is no need to remove it. An example embodiment comprises dexamethasone and benzyl benzoate. In this system, intravitreal levels of dexamethasone with a 25% formulation in 50 $\mu$l delivers a mean vitreous level of approximately 8.0 $\mu$g/ml over a three-month period. In comparison, a 25 $\mu$l injection delivers a mean vitreous level of approximately 4.0 $\mu$g/ml over a sixty day period. This composition is biocompatible, biodegradable, non-toxic, easy to manufacture, easy to deliver, and flexible in terms of therapeutic dose and duration of delivery.

A wide variety of other disease states are known by those of ordinary skill in the art, such as those described in Goodman & Gilman, THE PHARMACOLOGICAL BASIS OF THERAPEUTICS (McGraw Hill, 2001), and REMINGTON'S PHARMACEUTICAL SCIENCES (Lippincott Williams & Wilkins; 20th ed., 2000). Those to which the present invention may be applied may be determined by those with ordinary skill in the art without undue experimentation.

Suitable classes of active agents for use in the system of the present invention include, but are not limited to the following:

Peptides and proteins such as cyclosporin, insulins, glucagon-like-peptides, growth hormones, insulin related growth factor, botulinum toxins (Botox, Allergan), and heat shock proteins;

Anesthetics and pain killing agents such as lidocaine and related compounds, and benzodiazepam and related compounds;

Anti-cancer agents such as 5-fluorouracil, methotrexate and related compounds;

Anti-inflammatory agents such as 6-mannose phosphate;

Anti-fungal agents such as fluconazole and related compounds;

Anti-viral agents such as trisodium phosphomonoformate, trifluorothymidine, acyclovir, cidofovir, ganciclovir, DDI and AZT;

Cell transport/mobility impending agents such as colchicines, vincristine, cytochalasin B and related compounds;

Anti-glaucoma drugs such as beta-blockers: timolol, betaxolol atenolol;

Immunological response modifiers such as muramyl dipeptide and related compounds;

Steroidal compounds such as dexamethasone, prednisolone, and related compounds; and Carbonic anhydrase inhibitors.

In addition to the above agents, other active agents which are suitable for administration, especially to the eye and its surrounding tissues, to produce a local or a systemic physiologic or pharmacologic effect can be used in the system of the present invention. Examples of such agents include antibiotics such as tetracycline, chloramphenicol, ciprofloxacin, ampicillin and the like.

Any pharmaceutically acceptable form of the active agents of the present invention may be employed in the practice of the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

The active agents may also be used in combination with pharmaceutically acceptable carriers in additional ingredients such as antioxidants, stabilizing agents, and diffusion enhancers. For example, where water uptake by the active agent is undesired, the active agent can be formulated in a hydrophobic carrier, such as a wax or an oil, that would allow sufficient diffusion of the active agent from the system. Such carriers are well known in the art.

In another aspect of the invention, a low solubility active agent may be combined with a biodegradable, biocompatible excipient of higher solubility to result in an LSBB formulation. For example, dimethyl sulfone may be used as a binder in an LSBB formulation of a limited solubility active agent. Hence, the use of a soluble excipient in an LSBB formulation is within the scope of the present invention.

In one embodiment, the active agents, e.g., proteins, may be formulated in a glassy matrix of sugar which tends to protect the active agent from hydrolytic degradation and extend their shelf life and eliminate the need for cold storage. See, for example, Franks, *Long-Term Stabilization of Biologicals,* 12 Bio/Technology 253-56 (1994), the contents of which are hereby incorporated by reference.

Proteins may be formulated in a glass matrix by removing water from a homogeneous solution thereof. The water can be removed either by evaporation or by rapidly cold quenching the solution. The process is commonly referred to as vitrification. As water is removed from the solution, it becomes increasingly viscous until a "solidified" liquid containing the proteins is obtained. The "solidified" liquid is generically called glass.

Glasses have a number of unique physical and chemical properties which make them ideal for active agent formulation. Among them, the most important is that the solidified liquid retains the molecular disorder of the original solution. This disorder contributes to the glasses' long-term stability by preventing crystallization and chemical reactions of the proteins encased therein.

Sugars can also play an important part in stabilizing protein formulations. In solution, they are known to shift the denaturation equilibrium of proteins toward the native state. Most sugars, particularly low molecular weight carbohydrates, are also known to vitrify easily and to provide a glassy matrix that retards inactivating reactions of the proteins.

For illustrative purposes, the glassy sugar matrix for use in the system according to the present invention can be made by compressing a lyophilized mix of a protein with sugar and a buffer, and optionally, binders.

Examples of proteins and proteinaceous compounds which may be formulated and employed in the delivery system according to the present invention include those proteins which have biological activity or which may be used to treat a disease or other pathological condition. They include, but are not limited to growth hormone, Factor VII, Factor IX and other coagulation factors, chymotrypsin, trysinogen, alpha-interferon, beta-galactosidase, lactate dehydrogenase, growth factors, clotting factors, enzymes, immune response stimulators, cytokines, lymphokines, interferons, immunoglobulins, retroviruses, interleukins, peptides, somatostatin, somatotropin analogues, somatomedin-C, Gonadotropic releasing hormone, follicle stimulating hormone, luteinizing hormone, LHRH, LHRH analogues such as leuprolide, nafarelin and geserelin, LHRH agonists and antagonists, growth hormone releasing factor, callcitonin, colchicines, gonadotropins such as chorionic gonadotropin, oxytocin, octreotide, somatotropin plus and amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, secretin, pancreozymin, enkephalin, glucagons, and endocrine agents secreted internally and distributed by way of the bloodstream.

Other agents, such as $\alpha_1$ antitrypsin, insulin, glucagon-like-peptides, and other peptide hormones, botulinum toxins (Botox, Allergan), adrenal cortical stimulating hormone, thyroid stimulating hormone, and other pituitary hormones, interferons such as $\alpha$, $\beta$, and $\delta$ interferon, erythropoietin, growth factors such as GCSFm GM-CSF, insulin-like growth factor 1, tissue plasminogen activator, CF4, dDAVP, tumor necrosis factor receptor, pancreatic enzyes, lactase, interleukin-1 receptor antagonist, interleukin-2, tumor suppresser proteins, cytotoxic proteins, viruses, viral proteins, recombinant antibodies, portions of antibodies, and antibody fragments and the like may be used. Analogs, derivatives, antagonists, agonists, and pharmaceutically acceptable salts of the above may also be used.

Other active agents encompassed in the present invention include prodrugs. Because prodrugs are known to enhance numerous desirable qualities of pharmaceuticals (e.g., solubility, bioavailability, manufacturing, etc.) the pharmaceutical dosage forms of the present invention may contain compounds in prodrug form. Thus, the present invention is intended to cover prodrugs of the presently claimed active agents, methods of delivering the same, and compositions containing the same.

Analogues, such as a compound that comprises a chemically modified form of a specific compound or class thereof, and that maintains the pharmaceutical and/or pharmacological activities characteristic of said compound or class, are also encompassed in the present invention. Similarly, derivatives such as a chemically modified compound wherein the modification is considered routine by the ordinary skilled chemist, such as an ester or an amide of an acid, protecting groups, such as a benzyl group for an alcohol or thiol, and tert-butoxycarbonyl group for an amine, are also encompassed by the present invention.

The above agents are useful for the treatment or prevention of a variety of conditions including, but not limited to hemophilia and other blood disorders, growth disorders, diabetes, obesity, leukemia, hepatitis, renal failure, HIV infection, hereditary diseases such as cerebrosidase deficiency and adenoine deaminase deficiency, hypertension, septic shock, autoimmune disease such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal and other cancers, and management of bladder, prostatic, and pelvic floor disorders, and uterine fibroid (submucosal, subserosal, intramural, parasitic myomas, and seedling myomas) management (using for example but not limited to pirfenidone, human interferin-alpha, GNRH antagonists, Redoxifene, estrogen-receptor modulators). Additionally, the formulations of the present invention may be used to treat intracranial aneurysms by, for example, introducing fibrogen or plasmin.

It is further contemplated that topical formulations of these LSBBs with active agents can be applied for the transdermal administration of contraceptives, insulin or GLP-1, transdermal application for alopecia treatment or delivery of aspirin or other small molecules, smoking cessation agents, insulin, anti-obesity agents, antivirals (herpes therapies), agents for psoriasis therapies, agents for for alopecia therapies, agents for acne therapies, agents for erectile disfunction and anti-parasitic agents, to name a few.

The protein compounds useful in the formulations of the present invention can be used in the form of a salt, preferably a pharmaceutically acceptable salt. Useful salts are known to those skilled in the art and include salts with inorganic acids, organic acids, inorganic bases, or organic bases.

Sugars useful for preparing the glassy matrix discussed previously include, but are not limited to, glucose, sucrose, trehalose, lactose, maltose, raffinose, stachyose, maltodextrins, cyclodextrins, sugar polymers such as dextrans and their derivatives, ficoll, and starch.

Buffers useful for formulating the glassy matrix include, but not limited to MES, HEPES, citrate, lactate, acetate, and amino acid buffers known in the art.

The LSBB system comprising the glassy sugar matrix may be constructed of a bioerodible polymer with low water permeability. Such polymers include poly(glycolic acid), poly(lactic acid), copolymers of lactic/glycolic acid, polyorthoesters, polyanhydrides, polyphosphazones, polycaprolactone. These polymers may be advantageous because of their slow erosion properties and low water uptake; thus, they should not undergo undue changes during the course of the active agent delivery.

Naturally occurring or synthetic materials that are biologically compatible with body fluids suitable for use in the present invention generally include polymers such as polyethylene, polypropylene, polyethylene terephtalate, crosslinked polyester, polcarbonate, polysulfone, poly(2-pentene), poly(methylmethacrylate), poly(1,4-phenylene), polytetrafluoroethylene, and poly-ethylene-vinylacetate (EVA).

In an aspect of the present invention, the excipient is also biodegradable or bioerodible. As used herein, the terms "bioerodible" and "biodegradable" are equivalent and are used interchangeably. Biodegradable excipients are those which degrade in vivo, and wherein erosion of the excipient over time is required to achieve the agent release kinetics according to the invention. Suitable biodegradable excipients may include but are not limited to, for example, poly(glycolic acid), poly(lactic acid), copolymers of lactic/glycolic acid, polyorthoesters, polyanhydrides, polyphosphazones, polycarbonates, and polycaprolactone. The use of polylactic polyglycolic acid is described in, for example, U.S. Pat. No. 6,699,493. See also U.S. Pat. No. 5,869,079.

In another aspect of the invention, the excipient is biocompatible, meaning that it does not have undue toxicity or cause either physiologically or pharmacologically harmful effects. In another aspect of the invention, the excipient is biodegradable.

Examples of excipients that may be useful as biocompatible, biodegradable and/or bioerodible excipients in the present invention, as determined by one of ordinary skill in the art in light of this specification, without undue experimentation, include, but are not limited to:

d-α-tocopherol; d,l-α-tocopherol; d-β-tocopherol; d,l-β-tocopherol; d-η-tocopherol; and d,l-η-tocopherol (including acetate, hemisuccinate, nicotinate, and succinate-PEG ester forms of each of the foregoing); tocotrienol isomers, and their esters;

benzyl alcohol;
  benzyl benzoate;
  diethylene glycol dibenzoate;
  triethylene glycol dibenzoate;
  dibenzoate esters of poly(oxyethylene) diols of up to about 400 mwt;
  propylene glycol dibenzoate;
  dipropylene glycol dibenzoate;
  tripropylene glycol dibenzoate;
  dibenzoate esters of poly(oxypropylene) diols of up to about 3000 mwt;
  poly(oxypropylene) diols of up to about 3000 mwt;
  dimethyl sulfone;
  triethyl, tripropyl, and tributyl esters of O-acetylcitrate;
  triethyl, tripropyl, tributyl esters of citric acid; and
  liquid to semisolid polycarbonate oligomers, such as, but not limited to, those prepared by the polymerization of trimethylene carbonate [poly(1,3-propanediol carbonate)] or the ester exchange polymerization of diethylene carbonate with aliphatic diols or polyoxyalkane diols [poly(di-1,2-propylene glycol carbonate) or poly(tri-1,2-propylene glycol carbonate)].

Another example of biodegradable/biocompatible excipients useful in the present invention are "tocols." Tocols refers to a family of tocopherols and tocotrienals and derivatives thereof, because tocopherols and tocotrienals are derivatives of the simplest tocopherol, 6-hydroxy-2-methyl-2-phytyl-chroman. Tocopherols are also known as a family of natural or synthetic compounds commonly called Vitamin E. Alpha-tocopherol is the most abundant and active form of this class of compounds. Other members of this class include β-, γ-, and δ-tocopherols and α-tocopherol derivatives such as tocopheryl acetate, succinate, nicotinate, and linoleate. Useful tocotrienols include d-δ-tocotreinols, and d-β-, d-γ-tocotrienols, and their esters.

In addition to the excipients listed above, the following excipients having very low viscosities are valued not only by themselves as carriers of drugs for injectable sustained release (ISR) formulations, but also as additives to the ISR formulations of the excipients listed above to reduce their viscosities and therebye improve syringeability. These include: perfluorodecalin; perfluorooctane; perfluorohexyloctane; the cyclomethicones, especially octamethylcyclotetrasiloxane; decamethylcyclopentasiloxane, and dodecamethylcyclohexasiloxane polydimethylsiloxanes of viscosities below about 1000 cSt; diethyl carbonate; and dipropylcarbonate.

It is also contemplated that these liquid and solid LSBBs/active agent formulations can be coatings on implanted surfaces, such as but not limited to, those on catheters, stents (cardiac, CNS, urinary, etc.), prothesis (artificial joints, cosmetic reconstructions, and the like), tissue growth scaffolding fabrics, or bones and teeth to provide a wide variety of therapeutic properties (such as but not limited to, anti-infection, anti-coagulation, anti-inflammation, improved adhasion, improved tissue growth, improved biocompatibilty). These surfaces can be from a wide variety of materials, such as but not limited to, natural rubbers, wood, ceramics, glasses, metals, polyethylene, polypropylene, polyurethanes, polycarbonates, polyesters, poly(vinyl actetates), poly(vinyl alcohols), poly(oxyethylenes), poly(oxypropylenes), cellulosics, polypeptides, pblyacrylates, polymethacrylates, polycarbonates and the like.

Active agents, or active ingredients, that may be useful in the present invention, as determined by one of ordinary skill in the art in light of this specification without undue experimentation, include but are not limited to:

Analgesics, Anesthetics, Narcotics such as acetaminophen; clonidine (Duraclon Roxane) and its hydrochloride, sulfate and phosphate salts; oxycodene (Percolone, Endo) and its hydrochloride, sulfate, phosphate salts; benzodiazepine; benzodiazepine antagonist, flumazenil (Romazicon, Roche); lidocaine; tramadol; carbamazepine (Tegretol, Novartis); meperidine (Demerol, Sanofi-Synthelabo) and its hydrochloride, sulfate, phosphate salts; zaleplon (Sonata, Wyeth-Ayerst); trimipramine maleate (Surmontil, Wyeth-Ayerst); buprenorphine (Buprenex, Reckitt Benckiser); nalbuphine (Nubain, Endo) and its hydrochloride, sulfate, phosphate salts; pentazocain and hydrochloride, sulfate, phosphate salts thereof; fentanyl and its citrate, hydrochloride, ssulfate, phosphate salts; propoxyphene and its hydrochloride and napsylate salts (Darvocet, Eli Lilly& Co.); hydromorphone (Dilaudid, Abbott) and its hydrochloride, sulfate, and phosphate salts; methadone (Dolophine, Roxane) and its hydrochloride, sulfate, phosphate salts; morphine and its hydrochloride, sulfate, phosphate salts; levorphanol (Levo-dromoran, ICN) and its tartrate, hydrochloride, sulfate, and phosphate salts; hydrocodone and its bitartrate, hydrochloride, sulfate, phosphate salts;

Angiostatic and/or Anti-inflammatory Steroids such as anecortive acetate (Retaane®, Alcon, Inc., Fort Worth, Tex.); tetrahydrocortiso; 4,9(11)-pregnadien-17α,21-diol-3,20-dione (Anecortave) and its -21-acetate salt; 11-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its 21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide (Diamox®, Lederle Parenterals, Inc., Carolina, Puerto Rico; several other manufacturers); 21-nor-5β-pregnan -3α,17α,20-triol-3-acetate; 21-nor-5α-pregnan-3α,17α,20-triol-3-phosphate; 21-nor-5β-pregn -17(20)en-3α,16-diol; 21-nor-5β-pregnan-3α,17β,20-triol; 20-acetamide-21-nor-5β-pregnan -3α,17α-diol-3-acetate; 3βacetamido-5β-pregnan-11β,17α,21-triol-20-one-21-acetate; 21-nor-5α-pregnan-3α,17β,20-triol; 21α-methyl-5β-pregnan-3α,11β,17α,21-tetrol-20-one-21-methyl ether; 20-azido-21-nor-5β-pregnan-3α,17α-diol; 20(carbethoxymethyl)thio-21-nor-5β-pregnan -3α,17α-diol; 20-(4-fluorophenyl)thio-21-nor-5β-pregnan-3α,17α-diol; 16α-(2-hydroxyethyl) -17β-methyl-5β-androstan-3α,17αdiol; 20-cyano-21-nor-5β-pregnan-3α,17α-diol; 17α-methyl-5β-androstan-3α,17β-diol; 21-nor-5β-pregn-17(20) en-3α-ol; 21-or-5β-pregn-17(20)en-3α-ol-3-acetate; 21-nor-5-pregn-17(20)-en-3α-ol-16-acetic acid 3-acetate; 3β-azido-5β-pregnan -11β,17α,21-triol-20-one-21-acetate; and 5β-pregnan-11β,17α,21-triol-20-one; 4-androsten -3-one-17β-carboxylic acid; 17α-ethynyl-5(10)-estren-17β-ol-3-one; and 17α-ethynyl-1,3,5(10)-estratrien-3,17β-diol.

Nonsteroidal Anti-inflammatories such as naproxin; diclofenac; celecoxib; sulindac; diflunisal; piroxicam; indomethacin; etodolac; meloxicam; ibuprofen; ketoprofen; r-flurbiprofen (Myriad); mefenamic; nabumetone; tolmetin, and sodium salts of each of the foregoing; ketorolac bromethamine; ketorolac bromethamine tromethamine (Acular®, Allergan, Inc.); choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); methyl, ethyl, propyl, isopropyl, n-butyl, sec-butyl, t-butyl, esters of acetylsalicylic acid;

Angiogenesis Inhibitors such as squalamine, squalamine lactate (MSI-1256F, Genaear) and curcumin; Vascular Endothelial Growth Factor (VEGF) Inhibitors including pegaptanib (Macugen, Eyetech/Pfizer); bevacizumab (Avastin, Genentech/generic); Neovastat (Aeterna); PTK 787 (Schering/Novartis); Angiozyme (RibozymeChiron); AZD 6474 (AstraZeneca); IMC-1C11 (Imclone); NM-3 (ILEX Oncology); S6668 (Sugen/Pharmacia); CEP-7055 (Cephalon); and CEP-5214 (Cephalon); Integrin Antagonists such as Vitaxin (Applied Molecular Evolution/Medimmune); S 137 (Pharmacia); S247 (Pharmacia); ST 1646 (Sigma Tau); DPC A803350 (Bristol-Myers Squibb); and o-guanudines (3D Pharmaceuticals/generic); matrix metalloproteinase inhibitors such as prinomastat (AG 3340, Pfizer/generic), (ISV-616, InSite Vision), (TIMP-3, NIH); S3304 (Shionogi); BMS 275291 (Celltech/Bristol-Myers Squibb); SC 77964 (Pharmacia); ranibizumab (Lucentis, Genentech); ABT 518 (Abbott); CV 247 (Ivy Medical); shark cartilage extract (Neovastat, Aeterna); NX-278-L anti-VEGF aptamer (EyeTech); 2'-O-methoxyethyl antisense C-raf oncogene inhibitor (ISIS-13650); vitronectin and osteopontin antagonists (3-D Pharm); combretstatin A-4 phosphate (CA4P, Oxigene); fab fragment α-V/β-1 integrin antagonist (Eos-200-F, Protein Design Labs); α-v/β-3 integrin antagonist (Abbott); urokinase plasminogen activator fragment (A6, Angstrom Pharm.); VEGF antagonist (AAV-PEDF, Chiron); kdr tyrosine kinase inhibitor (EG-3306, Ark Therapeutics); cytochalasin E (NIH); kallikrinin-binding protein (Med. Univ. So. Carolina); combretastatin analog (MV-5-40, Tulane); pigment-epithelium derived growth factor (Med. Univ. SC); pigment-epithelium derived growth factor (Ad-PEDF, GenVec/Diacrin); plasminogen kringle (Med. Univ. SC); rapamycin; cytokine synthesis inhibitor/p38 mitogen-activated protein kinase inhibitor (SB-220025, GlaxoSmithKline); vascular endothelial growth factor antagonist (SP-(V5.2)C, Supratek); vascular endothelial growth factor antagonist (SU10944, Sugen/Pfizer); vascular endothelial growth factor antagonist (VEGF-R, Johnson & Johnson/Celltech); vascular endothelial growth factor antagonist (VEGF-TRAP, Regeneron); FGF1 receptor antagonist/tyrosine kinase inhibitor (Pfizer/Sugen); endostatin, vascular endothelial growth factor antagonist (EntreMed); bradykinin B1 receptor antagonist (B-9858, Cortech); bactericidal/permeability-increasing protein (BPI, Xoma); protein kinase C inhibitor (Hypericin, Kansai Med. U.); ruboxistaurinn mesylate (LY-333531, Eli Lilly & Co.); polysulphonic acid derivatives (Fuji Photo Film); growth factor antagonists (TBC-2653, TBC-3685, Texas Biotechnology); Tunica internal endothelial cell kinase (Amgen);

Anti-infective Agents such as Anti-bacterials including aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof; clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; rifampin; dapsone; atovaquone; rifabutin; linezolide; polymyxin B and its hydrochloride, sulfate, or phosphate salt; sulfacetamide and its sodium salt; minocycline; and clarithromycin;

Antifungals such as amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole;

Antimalarials such as chloroquine and its hydrochloride, sulfate or phosphate salt; hydroxychloroquine and its hydrochloride, sulfate or phosphate salt; mefloquine and its hydrochloride, sulfate, or phosphate salt; atovaquone; proguanil and its hydrochloride, sulfate, or phosphate salt forms;

Antituberculosis Agents such as ethambutol and its hydrochloride, sulfate, or phosphate salt forms; aminosalicylic acid; isoniazid; pyrazinamide'; ethionamide;

Antivirals such as amprenavir; interferon alfa-n3; interferon alfa-2b; interferon alfacon-1; peginterferon alfa-2b; interferon alfa-2a; lamivudine; zidovudine; amadine (Symmetrel, Endo) and its hydrochloride, sulfate, and phosphate salts; indinavir and its hydrochloride, sulfate, or phosphate salt; ganciclovir; ganciclovir sodium salt; famciclovir; rimantadine and its hydrochloride, sulfate, or phosphate salt; saquinavir mesylate; foscarnet; zalcitabine; ritonavir; ribavirin; zanamivir; delavirdine mesylate; efavirenz; amantadine and its hydrochloride, sulfate, or phosphate salt; palivizumab; oseltamivir and its hydrochloride, sulfate, or phosphate salt; abacavir and its hydrochloride, sulfate, or phosphate salt; valganciclovir and its hydrochloride, sulfate, or phosphate salt; valacyclovir and its hydrochloride, sulfate, or phosphate salt; didanosine; nelfinavir mesylate; nevirapine; cidofovir; acyclovir; trifluridine; penciclovir; zinc oxide; zinc salicylate; zinc salts of all isomers of tocopherol hemisuccnic acid; zinc salts of straight, branched, saturated, and unsaturated chain C2 to C20 aliphatic carboxylic acids; zinc pyruvate; zinc lactate; zinc ester complexes; and zinc acetoacetonate or zinc acetoacetic ester complexes;

Anti HIV/AIDS agents including stavudine, reverset (Pharmasset), ACH-126443 (Achillion), MIV-310 (Boehringer Ingelheim), ZeritIR(d4tT) (Bristol-Meyers Squibb), Ziagen (GlaxoSmithKline), Viroad (Glead), hivid (Roche), Emtriva (Gilead), delavirdine (Pfizer), AG-1549 (Pfizer), DPC-083 (Bristol-Myers Squibb), NSC-675451 (Advanced Life Sciences), IMC-125 (Tibitec), azidicarbonamide, GPG-NH2 (Tripep), immunitin (Colthurst), cytolin (Cytodyn), HRG-214 (Virionyx), MDX-010 (Gilead), TXU-PAP (Wayne Hughes Inst), proleukin (Chiron), BAY 50-4798 (Bayer), BG-777 (Virocell), Crixivan (Merck), Fuzeon (Hoff-La Roche), WF-10 (Oxo Chemie), Ad5 Gag vaccine (Merck), APIAOO-003 and 047 (Wyeth), Remunex (Immune Response Corp.), MVA-BN Nef (Bavarian Nordic), GTU MultyHIV vaccine (FIT Biotech);

Insulins such as Novolog (aspart), Novolin R, Novolin N, Novolin L, Novolin 70/30, and Novolog 70/30 (Novo Nordisk); Humalog (lispro) Humulin R, Humulin N, Humulin L, Humulin 50/50 and 70/30, and Humalog Mix 75/25 and 70/30 (Eli Lilly); Ultralente (Eli Lilly); Lantus (glargine, Aventis); porcine; and bovine insulins;

Glucagon-like Peptide-1 (Glp1) and analogs (for diabetes therapy and appetite suppression, cardiac protection) (see Keiffer et al., 20 Endocr Rev., 876-913 (1999); Glp1 Receptor stimulators such as exendin-4, Exenatide and Exenatide LAR (Amylin Pharma); Liraglutide (Novo Nordisk); ZP-10 (Zealnad Pharma); Glp-1-albumin (Conjuchem); and Dpp-IV inhibitors (which inhibit enzyme attack on Glp-1) such as LAF237 (Novartis); MK-0431 (Merck); BMS-477188 (Bristol-Myers Squibb); and GSK23A (GlaxoSmithKIine);

Alpha Androgenergic Agonist such as brimonidine tartrate; Beta Adrenergic Blocking Agents such as betaxolol and its hydrochloride, sulfate, or phosphate salt; levobetaxolol and its hydrochloride, sulfate, or phosphate salt; and timolol maleate;

Carbonic Anhydrase Inhibitors such as brinzolamide; dorzolamide and its drochloride, sulfate, or phosphate salt; and dichlorphenamid;

Mast Cell Stabilizers such as pemirolast and its potassium salt; nedocromil and its sodium salt; cromolyn and its sodium salt;

Miotics (Cholinesterase Inhibitors) such as demecarium bromide;

Prostaglandins such as bimatoprost; travoprost; and latanoprost;

Antihistamines such as olopatadine and its hydrochloride, sulfate, or phosphate salt forms; fexofenadine and its hydrochloride, sulfate, or phosphate salt; azelastine and its hydrochloride, sulfate, or phosphate forms; diphenhydramine and its hydrochloride, sulfate, or phosphate forms; and promethazine and its hydrochloride, sulfate, or phosphate forms;

Antimicrotubule Agents such as Taxoids including paclitaxel (Taxol, Bristol-Myers Squibb); vincristine (Oncovin, Eli Lilly & Co.) and its hydrochloride, sulfate, or phosphate salt forms; vinblastine (Velbe, Eli Lilly & Co.) and its hydrochloride, sulfate, or phosphate salt; vinorelbine (Novelbinr, Fabre/GSK); colchicines; docetaxel (Taxotere, Aventis); 109881 (Aventis); LIT 976 (Aventis); BMS 188797 (Bristol-Myers Squibb); BMS 184476 (Bristol-Myers Squibb); DJ 927 (Daiichi); DHA paclitaxel (Taxoprexin, Protarga); Epothilones including epothiloneB (EPO 906, Novartis/generic); BMS 247550 (Bristol-Myers Squibb); BMS 310705

(Bristol-Myers Squibb); epothilone D (KOS 862, Kosan/generic); and ZK EPO (Schering AG);

Antineoplastic agents such as doxorubicin and its hydrochloride, sulfate, or phosphate salt; idarubicin and its hydrochloride, sulfate, or phosphate salt; daunorubicin and its hydrochloride, sulfate, or phosphate salt; dactinomycin; epirubicin and its hydrochloride, sulfate, or phosphate salt; dacarbazine; plicamycin; mitoxantrone (Novantrone, OSI Pharmaceuticals) and its hydrochloride, sulfate, or phosphate salt; valrubicin; cytarabine; nilutamide; bicalutamide; flutamide; anastrozole; exemestane; toremifene; femara; tamoxifen and tamoxifen citrate; temozolimide (Temador); gemcitabine and its hydrochloride, sulfate, or phosphate salt; topotecan and its hydrochloride, sulfate, or phosphate salt; vincristine and its hydrochloride, sulfate, or phosphate salt; liposomal vincristine (Onco-TCS, Inex/Elan); methotrexate and methotrexate sodium salt; cyclophosphamide; estramustine sodium phosphate; leuprolide and leuprolide acetate; goserelin and goserelin acetate; estradiol; ethinyl estradiol; Menest esterified estrogens; Premarin conjugated estrogens; 5-flurouracil; bortezamib (Velcade, Millenium Pharmaceuticals);

Antiapoptotics such as desmethyldeprenyl (DES, RetinaPharma);

Aldose Reductase Inhibitors such as GP-1447 (Grelan); NZ-314 (parabanic acid derivative, Nippon Zoki); SG-210 (Mitsubishi Pharma/Senju); and SJA-7059 (Senju);

Antihypertensives such as candesartan cilexetil (Atacand/Biopress, Takeda/AstraZeneca/Abbott); losartan (Cozaar, Merck); and lisinopril (Zestril/Prinivil, Merck/AstraZeneca);

Antioxidants such as benfotiamine (Albert Einstein Col. Of Med./WorWag Pharma); ascorbic acid and its esters; tocopherol isomers and their esters; and raxofelast (IRFI-005, Biomedica Foscama);

Growth Hormone Antagonists such as octreotide (Sandostatin, Novartis); and pegvisomant (Somavert, Pfizer/Genentech);

Vitrectomy Agents such as hyaluronidase (Vitrase, ISTA Pharm./Allergan);

Adenosine Receptor Antagonist such as A2B adenosine receptor antagonist (754, Adenosine Therapeutics);

Adenosine Deaminase Inhibitor such s pentostatin (Nipent, Supergen);

Glycosylation Antagonists such as pyridoxamine (Pyridorin, Biostratum);

Anti-Ageing Peptides, such as Ala-Glu-Asp-Gly (Epitalon, St Petersburg Inst. Bioreg. and Geron);

Topoisomerase Inhibitors such as doxorubicin (Adriamycin/Caelyx, Pharmacia/generics); daunorubicin (DaunoXome, Gilead/generics); etoposide (Vepecid/Etopophos, Bristol-Myers Squibb/generics); idarubicin (Idamycin, Pharmacia); irinotecan (Camptosar, Pharmacia); topotecan (Hycamtin, GlaxoSmithKline); epirubicin (Ellence, Phamacia); and raltitrexed (Tomudex, AstraZeneca);

Anti-metabolites such as methotrexate (generic) and its sodium salt; 5-fluorouracil (Adrucil, ICN Pharmacia); cytarabine (Cytosar, Pharmacia/generic); fludarabine (Fludara, Schering) and its forms as salts with acids; gemcitabine (Gemsar, Eli Lilly& Co.); capecitabine (Xeloda, Roche); and perillyl alcohol (POH, Endorex);

Alkylating Agents such as chlorambucil (Leukeran, GlaxoSmithKline); cyclophosphamide (Cytoxan, Pharmacia/Bristol-Meyers Squibb); methchlorethanine (generic); cisplatin (Platinal, Pharmacia/Bristol-Meyers Squibb); carboplatin (Paraplatin, Bristol-Myers Squibb); temozolominde (Temodar) and oxaliplatin (Sanofi-Synthelabs);

Anti-androgens such as flutamide (Eulexin, AstraZeneca); nilutamide (Anandron, Aventis); bicalutamide (Casodex, AstraZeneca);

Anti-oestrogens such as tamoxifen (Nolvadex, AstraZeneca); toremofine (Fareston, Orion/Shire); Faslodex (AstraZeneca); arzoxifene (Eli Lilly & Co.); Arimidex (AstraZeneca); letrozole (Femera, Novartis); Lentaron (Novartis); Aromasin (Pharmacia); Zoladex (AstraZeneca); lasoxifene (CP-366,156, Pfizer); ERA-923 (Ligand/Wyeth); DCP 974 (DuPont/Bristol Myers Squibb); ZK 235253 (Shering AG); ZK1911703 (Shering AG); and ZK 230211 (Shering AG);

Oncogene Activation Inhibitors, including for example, Bcr-Abl Kinase Inhibition such as Gleevec (Novartis); Her2 Inhibition such as trastuzumab (Herceptin, Genentech); MDX 210 (Medarex); E1A (Targeted Genetics); ME103 (Pharmexa); 2C4 (Genentech); C1-1033 (Pfizer); PKI 166 (Novartis); GW572016 (GlaxoSmithKIine) and ME104 (Pharmexa); EGFr Inhibitors such as Erbitux (Imclone/Bristol-Myers Squibb/Merck KgaA); EGFr Tyrosine Kinase Inhibitors such as gefitinib (Iressa ZD 1839, AstraZeneca); cetuximab (Erbitux, Imclone/BMS/Merck KGaA); erlotinib (Tarceva, OSI Pharmaceutical/Genentech/Roche); ABX-EGF (Abgenix); C1-1033 (Pfizer); EMD 72000 (Merck KgaA); GW572016 (GlaxoSmithKline); EKB 569 (Wyeth); PKI 166 (Novartis); and BIBX 1382 (Boehringer Ingleheim); Farnesyl Transferase Inhibitors such as tipifamib (Zarnestra, Johnson & Johnson); ionafarnib (Sarasar, Schering-Plough); BMS-214,662 (Bristol-Myers Squibb); AZ3409 (AstraZeneca); CP-609,754 (OSI Pharmaceuticals); CP-663,427 (OSI Pharmaceuticals/Pfizer); Arglabin (NuOncology); RPR-130401 (Aventis); A 176120 (Abbott); BIM 46228 (Biomeasure); LB 42708 (LG Chem); LB 42909 (LG Chem); PD 169451 (Pfizer); and SCH226374 (Schering-Plough); Bcl-2 Inhibitors such as BCL-X (Isis); ODN 2009 (Novartis); GX 011 (Gemin X); and TAS 301 (Taiho); Cyclin Dependent Kinase Inhibitors such as flavopiridol (generic, Aventis); CYC202 (Cyciacel); BMS 387032 (Bristol-Myers Squibb); BMS 239091 (Bristol-Myers Squibb); BMS 250904 (Bristol-Myers Squibb); CGP 79807 (Novartis); NP102 (Nicholas Piramal); and NU 6102 (AstraZeneca); Protein Kinase C Inhibitors such as Affinitac (Isis, Eli Lilly & Co.); midostaurin (PKC 412, Novartis/generic); bryostatin (NCI/GPC Biotech/generic); KW 2401 (NCI/Kyowa Hakko); LY 317615 (Eli Lilly & Co.); perifosine (ASTA Medica/Baxter/generic); and SPC 100840 (Sphinx);

Telomerase Inhibitors such as GRN163 (Geron/Kyowa Hakko) and G4T 405 (Aventis);

Antibody Therapy including Herceptin (Genentech/Roche); MDX-H210 (Medarex); SGN-15 (Seattle Genetics); H11 (Viventia); Therex (Antisoma); rituximan (Rituxan, Genentech); Campath (ILEX Oncology/Millennium/Shering); Mylotarg (Celltech/Wyeth); Zevalin (IDEC Pharmaceuticals/Schering); tositumomab (Bexxar, Corixa/SmithKline Beecham/Coulter); epratuzumab (Lymphocide, Immunomedics/Amgen); Oncolym (Techniclone/Schering AG); Mab Hu1D10 antibody (Protein Design Laboratories); ABX-EGF (Abgenix); infleximab (Remicade®, Centocor) and etanercept (Enbrel, Wyeth-Ayerst);

Antisense Oligonucleotides such as Affinitac (Isis Pharmaceuticals/Eli Lilly & Co.); and Genasence (Genta/Aventis);

Fusion Proteins such as denileukin diftitox (Ontak, Ligand);

Luteineizing Hormone Releasing Hormone (LHRH) Agonists aka Gonadotropin Releasing Hormone (GnRH) Agonists such as goserelin (Zoladex, AstraZeneca); leuporelin (Lupron, Abbott/Takeda); leuporelin acetate implant (Viadur, ALZA/Bayer and Atigrel/Eligard, Atrix/Sanofi-Synthelabo); and triptorelin (Trelstar, Pharmaceuticals);

Tyrosine Kinase Inhibitors/Epidermal Growth Factor Receptor Inhibitors such as gefitinib (Iressa, AstraZeneca, ZD 1839); trastuzumab (Herceptin, Genentech); erlotinib (Tarceva, OSI Pharmaceuticals, OSI 774); cetuximab (Erbitux, Imclone Systems, IMC 225); and pertuzumab (Omnitarg, Genentech, 2C4);

Ribonucleotide Reductase Inhibitors such as gallium maltolate (Titan);

Cytotoxins such as Irofulven (MGI 114, MGI Pharma);

IL2 Therapeutics such as Leuvectin (Vical);

Neurotensin Antagonist such as SR 48692 (Sanofi-Synthelabo);

Peripheral Sigma Ligands such as SR 31747 (Sanofi-Synthelabo);

Endothelin ETA/Receptor Antagonists such as YM-598 (Yamanouchi); and atrasentan (ABT-627, Abbott);

Antihyperglycemics such as metformin (Glucophage, Bristol-Myers Squibb) and its hydrochloride, sulfate, phosphate salts; and miglitol (Glyset, Pharmacia/Upjohn);

Anti-glaucoma Agents such as dorzolamide (Cosopt, Merck); timolol; betaxolol and its hydrochloride, sulfate, phosphate salts; atenolol; and clorthalidone;

Anti-(Chromatin Modifying Enzymes) such as suberoylanilide hyroxaxamic acid (Aton/Merck);

Agents for Obesity Management, such as glucagon-like-peptides, phendimettrazine and its tartrate, hydorochloride, sulfate, phosphate salts; methamphetamine and its hydrochloride, sulfate, phosphate salts; and sibutramine (Meridia, Abbott) and its hydochloride, sulfate, phosphate salts;

Treatments for Anemia such as epoetin alpha (Epogen, Amgen); epoetin alpha (Eprex/Procrit, Johnson & Johnson); epoetin alpha (ESPO, Sankyo and Kirin); and darbepoetin alpha (Aranesp, Amgen); epoetin beta (NeoRecormon, Roche); epoetin beta (Epogen, Chugai); GA-EPO (Dynepo, TKT/Aventis); epoetin omega (Elanex/Baxter); R 744 (Roche); and thrombopoetin (Genetech/Pharmacia);

Treatments for Emesis such as promethazine (Phenergan, Wyeth); prochlorperazine; metoclopramide (Reglan, Wyeth); droperidol; haloperidol; dronabinol (Roxane); ondasetron (Zofran, GlaxoSmithKiine); ganisetron (Kytril, Roche); dolasetron (Anzemet, Aventis); indisetron (NN-3389, Nisshin Flour/Kyorin); aprepitant (MK-869, Merck); palonosetron (Roche/Helsinn/MGI Pharma); lerisetron (FAES); nolpitantium (SR 14033, Sanofi-Synthelabo); R1124 (Roche); VML 670 (Vemalis, Eli Lilly & Co.); and CP 122721 (Pfizer);

Neutropaenia Treatments such as filgrastim (Neupogen, Amgen); leukine (Immunex/Schering AG); filgrastim-PEG (Neulasta, Amgen); PT 100 (Point Therapeutics); and SB 251353 (GlaxoSmithKline);

Tumor-induced Hypercalcaemia Treatments such as Bonviva (GlaxoSmithKline); ibandronate (Bondronat, Roche); pamidronate (Aredia, Novartis); zolendronate (Zometa, Novartis); clodronate (Bonefos, generic); incadronate (Bisphonal, Yamanouchi); calcitonin (Miacalcitonon, Novartis); minodronate (YM 529/Ono 5920, Yamanouchi/Ono); and anti-PTHrP (CAL, Chugai);

Blood Anticoagulants such as Argathroban (GlaxoSmithKiine); warfarin (Coumadin, duPont); heparin (Fragmin, Pharmacia/Upjohn); heparin (Wyeth-Ayerst); tirofiban (Aggrastat, Merck) and its hydrochloride, sulfate, phosphate salts; dipyridamole (Aggrenox, Boehringer Ingelheim); anagrelide (Agrylin, Shire US) and its hydrochloride, sulfate, phosphate salts; epoprostenol (Flolan, GlaxoSmithKline) and its hyrochloride, sulfate, phosphate salts; eptifibatide (Integrilin, COR Therapeutics); clopidogrel (Plavix, Bristol-Myers Squibb) and its hydrochloride, sulfate, or phosphate salts; cilostazol (Pletal, Pharmacia/Upjohn); abciximab (Reopro, Eli Lilly & Co.); and ticlopidine (Ticlid, Roche);

Immunsuppressive Agents such as sirolimus (rapamycin, Rapamune®, Wyeth-Ayerst); tacrolimus (Prograf, FK506); and cyclosporins;

Tissue Repair Agents such as Chrysalin (TRAP-508, Orthologic-Chrysalis Biotechnology);

Anti-psoriasis Agents such as anthralin; vitamin D3; cyclosporine; methotrexate; etretinate, salicylic acid; isotretinoin; and corticosteroids;

Anti-acne Agents such as retinoic acid; benzoyl peroxide; sulfur-resorcinol; azelaic acid; clendamycin; erythromycin; isotretinoin; tetracycline; minocycline;

Anti-skin parasitic Agents such as permethrin and thiabendazole;

Treatments for Alopecia such as minoxidil and finasteride;

Contraceptives such as medroxyprogesterone; norgestimol; desogestrel; levonorgestrel; norethindrone; norethindrone; ethynodiol; and ethinyl estradiol;

Treatments for Smoking Cessation including nicotine; bupropion; and buspirone;

Treatments for Erectile Disfunction such as alprostadil; and Sildenafil;

DNA-alkyltranferase Agonist including temozolomide;

Metalloproteinase Inhibitor such as marimastat;

Agents for management of wrinkles, bladder, prostatic and pelvic floor disorders such as botulinum toxin;

Agents for management of uterine fibroids such as pirfenidone, human interferin-alpha, GnRH antagonists, Redoxifene, estrogen-receptor modulators;

Transferrin Agonist including TransMID (Xenova Biomedix); Tf-CRM107 (KS Biomedix);

Interleukin-13 Receptor Agonist such as IL-13-PE38QQR (Neopharm);

Nucleic acids such as small interfering RNAs (siRNA) or RNA interference (RNAi), particularly, for example siRNAs that interfere with VEGF expression;

and Psychotherapeutic Agents including Anti-anxiety drugs such as chlordiazepoxide; diazepam; chlorazepate; flurazepam; halazepam; prazepam; clorazepam; quarzepam; alprazolam; lorazepam; orazepam; temazepam; and triazolam; and Anti-psychotic drugs such as chlorpromazine; thioridazine; mesoridazine; trifluorperazine; fluphenazine; loxapine; molindone; thiothixene; haloperidol; pimozide; and clozapine.

Those of ordinary skill in the art will appreciate that any of the foregoing disclosed active agents may be used in combination or mixture in the pharmaceutical formulations of the present invention. Such mixtures or combinations may be delivered in a single formulation, or may be embodied as different formulations delivered either simultaneously or a distinct time points to affect the desired therapeutic outcome. Additionally, many of the foregoing agents may have more than one activity or have more than one therapeutic use, hence the particular category to which they have been ascribed herein is not limiting in any way. Similarly, various biodegradable, biocompatible excipients may be used in combination or in mixtures in single or multiple formulations as required for a particular indication. These mixtures and combinations of active agents and excipients may be determined without undue experimentation by those of ordinary skill in the art in light of this disclosure.

The formulations of the present invention may be sterilized for use by methods known to those of ordinary skill in the art. Autoclaving and e-beam have been used in informal studies of several embodiments and have not appeared to have significant impact. Similarly, informal stability studies indicate acceptable stability of several embodiments. Additionally, reproducibility between aliquots and lots is very good, with a standard deviation of less than five percent or better. Hence, standard pharmaceutical manufacturing techniques are readily applied to the technologies described herein.

An example embodiment of the present invention comprises the active agent dexamethasone and the excipient benzyl benzoate. Dexamethasone is a glucocorticoid and typically used in the form of the acetate or disodium phosphate ester. Glucocorticoids are adrenocortical steroids suppressing the inflammatory response to a variety of agents that can be of mechanical, chemical or immunological nature. Administration of dexamethasone can be topical, periocular, systemic (oral) and intravitreal. Doses vary depending on the condition treated and on the individual patient response. In ophthalmology, dexamethasone sodium phosphate (Decadron®, Merck & Co.) as a 0.1% solution has been widely used since its introduction in 1957. The ophthalmic dose depends on the condition treated. For control of anterior chamber inflammation, the topical dose is usually 1 drop, 4 times a day for up to a month following surgery (around 0.5 mg per day). For control of posterior segment inflammation, periocular injections of 4 mg of dexamethasone, or daily oral administration of 0.75 mg to 9 mg of dexamethasone in divided doses are not uncommon. Intravitreal injections of 0.4 mg of dexamethasone have been administered in conjunction with antibiotics for the treatment of endophthalmitis.

Benzyl benzoate (CAS 120-51-4, FW 212.3). In the past, the oral administration of benzyl benzoate was claimed to be efficacious in the treatment of intestinal, bronchial, and urinary ailments, but its use has been superseded by more effective drugs. Presently, it is topically applied as a treatment for scabies and pediculosis. Goodman & Gilman's THE PHARMACOLOGICAL BASIS OF THERAPEUTICS 1630 (6th ed., 1980); FDA approval, Fed Reg. 310.545(a)(25)(i). Benzyl benzoate is approved in minor amounts in foods as a flavoring (FDA, Title 21, vol. 3, ch I, subch B, part 172(F), §172.515), and as a component in solvents for injectable drug formulations (see, e.g., Faslodex® and Delestrogen®).

Benzyl benzoate is a relatively nontoxic liquid which when applied topically in the eye results in no damage. Grant, TOXICOLOGY OF THE EYE 185 (2d ed., 1974). Its oral $Ld_{50}$ in humans is estimated to be 0.5 g/kg-5.0 g/kg. Gosselin et al., II CLIN TOX OF COMMERCIAL PROD. 137 (4th ed., 1976). In vivo, benzyl benzoate is rapidly hydrolyzed to benzoic acid and benzyl alcohol. The benzyl alcohol is subsequently oxidized to benzoic acid, which is then conjugated with glucuronic acid and excreted in the urine as benzoylglucuronic acid. To a lesser extent, benzoic acid is conjugated with glycine and excreted in the urine as hippuric acid. HANDBOOK OF PESTICIDE TOXICOLOGY 1506 (Hayes & Laws, eds., 1991).

Dexamethasone, when mixed with benzyl benzoate, forms a uniform suspension. A formulation of 25% is easily syringeable. When the suspension is slowly injected into the posterior segment of the eye, for example, a uniform spherical deposit (reservoir) is formed in the vitreous body. The reservoir maintains its integrity and in vivo "breakage" has not been obverved ophthalmoscopically. Dexamethasone is then released slowly into the vitreous humor of the posterior segment. Dexamethasone and benzyl benzoate are eventually metabolized to byproducts that are excreted in the urine.

Similarly, triamcinolone acetonide (TA) in benzyl benzoate forms a syringeable suspension that retains its integrity and in vivo. In rabbit studies involving intraocular injection of TA/benzyl benzoate formulations, described below, near zero-order release of TA has been observed in vivo for more than one year (data not shown). Smaller doses result in more-rapid release profiles, such that the TA is released over a six-month period (data not shown). Both Dex and TA formulations may be useful in treating the eye following cateract surgery or replacement.

An aspect of the invention provides for a composition comprising an active agent and the LSBB excipient useful for the treatment of iris neovascularization from cataract surgery, macular edema in central retinal vein occlusion, cellular transplantation (as in retinal pigment cell transplantation), cystiod macular edema, psaudophakic cystoid macular edema, diabetic macular edema, pre-phthisical ocular hypotomy, proliferative vitreoretinopathy, proliferative diabetic retinopathy, exudative age-related macular degeneration, extensive exudative retinal detachment (Coat's disease), diabetic retinal edema, diffuse diabetic macular edema, ischemic ophthalmopathy, chronic focal immunalogic corneal graft reaction, neovascular glaucoma, pars plana vitrectomy (for proliferative diabetic retinopathy), pars plana vitrectomy for proliferatve vitreoretinopathy, sympathetic ophthalmia, intermediate uveitis, chronic uveitis, intraocular infection such as endophthalmitis, Irvine-Gass syndrome.

Another embodiment of the invention provides to formulations and uses of the tocopherols and/or tocotrienols and their esters with the insulins for the transdermal delivery of the insulins in the management of diabetes. Tocopherols and/or the tocotrienols and their esters possess outstanding capabilities to carry therapeutic agents, especially moderate molecular weight proteins such as the insulins, through the skin into the body. Indeed, it is contemplated that wide variety of other therapeutic agents (such as: steroids, NSAIDs, antibiotics, hormones, growth factors, anti-cancer agents, etc) may be available for effective transdermal delivery formulations with the tocopherols and/or tocotrienols and their esters.

The advantages to bypassing oral drug delivery that allow the enzymatic transformations of the liver and the digestive processes of the gut (and also engender gastric distresses) have inspired research to find alternative methods. A prime example is insulin therapy for diabetes. Several tutorials and reviews of the present state of insulin therapies are: Owens, 1 Nature Reviews/Drug Discovery 529-540 (2002); Cefalu, 113(6A) Am J Med 25S-35S (2002); Nourparvar et al., 25(2) Trends Pharmacol Sci, 86-91 (2004). Avoidance of daily multiple painful subcutaneous injections has led to alternative routes such as buccal/sublingual, rectal, intranasal, pulmonary, and transdermal. Yet no completely acceptable alternatives to injection have been established. Most promising are pulmonary systems (Exubra, Pfizer/Aventis; AERxiDMS, Aradigm/Novo Nordisk) and as disclosed here novel transdermal delivery formulations involving the tocopherols and/or tocotrienols and their esters as penetrating vehicles for therapeutic agents.

The desirability of simple and painless transdermal delivery of insulin and other therapeutic agents has inspired a number of transdermal approaches (iontophoresis (electrical charge); phonophoresis (ultrasound); photoenhancement (pulsed laser); heat; transfermers (lipid vesicles); and penetrating agents (DMSO, NMP. etc.)) over the years with incomplete results. Transdermal delivery is considered to be hindered by the skin's relatively impermeability to large hydrophilic polypeptides such as insulin. The present invention, however, provides effective levels of insulin delivered in a sustained release fashion into the bloodstream when applied as intimate mixtures with α-tocopheryl acetate onto the skin. In a mouse model, effective levels of insulin were delivered in a sustained release fashion into the bloodstream of a mouse when applied as intimate mixtures with α-tocopheryl acetate onto the mouse skin.

Because tocopherols have long been ingredients in sunscreen and cosmetic formulations, there are numerous references in the literature to the tocopherols' being applied to the skin and demonstrations of their migrating through the skin. See e.g., Zondlo, 21(Suppl 3) Int J Toxicol, 51-116 (2002). These reports show the ease and safety with which the tocopherols can penetrate skin, but none disclose any use of the tocopherols as penetration enhancers or carriers of therapeutic agents through the skin into the body. Indeed, a recent review of 102 chemical penetration enhancers for transdermal drug delivery did not mention the tocopherols or tocotrienols. Karande et al., 102(13) Proc Natl Acad Sci USA, 4688-93 (2005).

Tocopherol formulations that allow the facile and effective transport of therapeutic agents through the skin into the body may employ d, l , and dl isomers of alpha, beta, gamma and delta tocopherols and their esters (formates, acetates, propionates, $C_4$ to $C_{20}$ straight and branched chain aliphatic acid esters, maleates, malonates, fumarates, succinates, ascorbates, and nicotinates); d, l , and dl isomers of alpha, beta, gamma, and delta tocotrienols and their esters (formates, acetates, propionates, $C_4$ to $C_{20}$ straight and branched chain aliphatic acid esters, maleates, malonates, fumarates, succinates, ascorbates and nicotinates).

Another embodiment of the present invention, further related to the tocopherols, provides to formulations of 2-acetyloxy benzoic acid and its aliphatic esters with tocopherols and tocotrienols and licorice extracts. In particular, this aspect provides for injectable, ingestable or topical formulations employing the tocopherols and/or tocotrienols and/or licorice extracts with 2-acetyloxybenzoic acid (2-ABA) and certain of its aliphatic esters allow all the well known medicinal benefits of 2-ABA and its aliphatic esters while substantially avoiding the gastric toxicities normally associated with the ingestion of 2-ABA itself.

Unlike the more recently developed specific COX-2 inhibiting nonsteroidal anti-inflammatories such as celecoxib, rofecoxib, and the like, there is the confidence that decades of pharmaceutical experience with 2-ABA have well defined its benefits and disadvantages. The full benefits and problems of the specific COX-2 inhibitors are still being discovered. In the case of the "traditional" NSAIDs such as 2-ABA, ibuprofen, naproxen, ketoprofen, diclofenac, indimethacin, etc., evidence accumulates on the damage they do to the stomach and small bowel. Although the specific COX-2 inhibitors have demonstrated lower gastrointestinal problems than 2-ABA, serious cardiovascular problems associated with specific COX-2 inhibitors are surfacing. As for 2-ABA, its general analgesic anti-inflammatory benefits are legendary; and as the chemistries of both of its COX-1 and COX-2 inhibitions are revealed the cardioprotective properties associated with its COX-1 inhibition are in striking contrast to the cardiovascular safety problems of the COX-2 only inhibitors. The reason for 2-ABA's gastrointestinal toxicity has been ascribed to its COX-1 inhibition. And indeed the lower order of gastrointestinal problems of celecoxib, rofecoxib, and the like is seen to be due to their COX-2 only inhibition. But, interestingly the normal intestinal appearances in the COX-1 knockout animals point to more subtle reasons for 2-ABA's gastrointestinal toxicity. The concomitant inhibition of both COX-1 and 2 enzymes may be the problem.

Whatever the mechanisms for 2-ABA's gastrointestinal toxicity, the well demonstrated benefits of 2-ABA in other areas of the body are incentives to seek ways to get the molecule past the gut without damage. Of course injection or topical application avoid the gut, but the major mode of administration is ingestion. Three distinctly different methods of lowering the gut irritation of ingested 2-ABA have been reported. The first, and most successful, is the discovery in studies in rats and pigs by Rainsford and Whitehouse reported in 1980 (10(5) Agents and Actions, 451-56) that the methyl, ethyl, and phenyl esters of 2-ABA elicit practically no gastric ulcerogenic activity and yet still have nearly all the anti-inflammatory properties of 2-ABA. Surprisingly, the investigation of oral administrations of the esters of 2-ABA has not been pursued further. Topical applications of 2-ABA esters for acne control, sunscreen, and placating insect bites have been reported. See U.S. Pat. Nos. 4,244,948 , 4,454,122, and 3,119,739. The second method of reducing 2-ABA gastric distress recommends diets rich in tocopherols and/or tocotrienols, resulting ing about a 30% to 40% reduction in lesion formation which is not as extensive as that provided by 2-ABA esters. See e.g., Jaarin et al., 13(Suppl) Asia Pac J Clin Nutr, 5170 (2004); Nafeeza et al., 11(4) Asia Pac J Clin Nutr 309-13 (2002); Sugimoto et al., 45(3) Dig Dis Sci, 599-605 (2000); Stickel et al, 66(5) Am J Clin Nutr 1218-23 (1997). The third method of reducing gastric stress is by the concomitant oral administration of licorice extract (glycyrrhizin) with 2-ABA. Rainsford & Whitehouse, 21 Life Sciences 371-78 (1977); Dehpour et al., 46 J Pharm Pharmacol 148-49 (1994). This gave 66% to 80% reduction in ulceration compared to 2-ABA alone. Formulations combining 2-ABA or its esters, the tocopherols (or their acetates) and/or tocotrienols (or their acetates), and licorice extracts all together have not been tried.

Treatment of inflammatory conditions of the eye or joints by direct injection avoids gastric distress and the inefficient systemic exposure of the ingestion route. Ingestion in humans of the commonly prescribe dosages of 2-ABA (0.650-1.3 g) leads to combined 2-ABA/2-hydroxy benzoic acid (2-HBA) levels in the plasma of about 20-100 μg/ml. Kralinger et al., 35 Ophthalmic Res 107 (2003). Studies in rabbit eyes indicate that at these plasma levels the concentration of 2-ABA/2-HBA in the vitreous is in the range of 5-10 μg/ml. The 2-ABA level is much lower than 2-HBA since within 30 minutes in the plasma about 97% of the 2-ABA is hydrolyzed to 2-HBA. Once remaining 2-ABA reaches the vitreous its rate of hydrolysis in that environment is greatly reduced. There an initial level of 4 μg/ml is halved in 1.5-2 hours. the half-life of 2-HBA is not well defined since its initial concentration is increased by the conversion of 2-ABA to 2-HBA; but the half life is probably twice that of 2-ABA. Valeri et al., 6(3) Lens & Eye Toxicity Res 465-75 (1989). This highlights another advantage of direct injection over oral (systemic) administration: injection avoids the substantial loss of the acetyl group in the hydrolysis of 2-ABA before it reaches its target. It has been shown that the major method of 2-ABA's anti-inflammatory action is its ability deactivate the COX 1&2 enzymes by irreversibly inserting its acetyl group into these enzymes. Roth & Majerus, 56 J Clin Invest 624-32 (1975). The ID50 for this reaction in the eye has been determined to be in the range of 0.9-9.0 μg/ml. Higgs et al, 6(Suppl) Agents & Actions 167-75 (1979). Kahler et al., 262(3) Eur J Pharmacol 261-269 (1994).

One example of an injectable sustained release (ISR) 2-ABA formulation in the eye is the injection of a 1.0 ml tamponade of silicone oil containing 1.67 mg into rabbit eye vitreous chamber. Only 2-HBA was measured in the study, which observed an initial burst of 640 μg/ml within 6 hours.

2-HBA decreased to 20 µg/ml in 20 hours and 5 µg/ml after 120 hours. Kralinger et al., 21(5) Retina 513-20 (2001). The use of the ethyl ester of 2-ABA in ISR formulations should give longer half lives (longer sustained deliveries) than 2-ABA since the ester is more hydrophobic. Also, the incorporation of 2-ABA esters or 2-ABA into hydrophobic excipients such as the tocopherols (or their acetates) or the tocotrienols (or their acetates) should lead to longer sustained deliveries.

A study of the distribution of 2-ABA and 2-HBA in the blood and synovial fluid (human knee) from ingested 650 mg doses of 2-ABA showed the maximum plasma levels of 3.3 µg/ml 2-ABA in 7.7 minutes and 23 µg/ml 2-HBA in 10.9 minutes. Maximum synovial fluid levels were 2.5 µg/ml 2-ABA in 19.4 minutes and 14.5 µg/ml 2-HBA in 21.9 minutes. Soren, 6(1) Scand J Rheumatol 17-22 (1977). The 2-ABA was gone in the blood in 75 minutes and gone in the synovial fluid in 2.3 to 2.4 hours. A study of intra-articular injections of 20 µg/ml 2-ABA in the 33 ml of synovial fluid in the adult human knee also revealed that the average half life of combined 2-ABA/2-HBA was 2.4 hours. Owen et al., 38 Br J clin Pharmac 347-55 (1994); Wallis et al., 28 Arthritis Rheum 44149 (1985).

In addition to the references noted above relating to anti-inflammation therapies involving topical applications of 2-ABA ester formulations, there are the references referring to 2-ABA esters (U.S. Pat. No. 3,119,739, U.S. Patent Application Pub. No. 2002-0013300) or 2-ABA (U.S. Pat. No. 4,126,681) as analgesics for skin irritations and wound healing. Other reports, however, reveal poor results with topically applied 2-ABA to relieve pain from insect bites (Balit et al., 41(6) Toxicol Clin Toxicol 801-08 (2003)) or allergic reactions (Thomsen et al., 82 Acta Derm Venereal 30-35 (2002)). Better results were found on dermal applications of chloroform solutions of 2-ABA (Kochar et al., 47(4) J Assoc Physicians India 33740 (1999)) or slurries of 2-ABA in a commercial skin moisturizer (Balakrishnan et al., 40(8) Int J Dermatol 535-38 (2002)) to alleviate the pain of acute herpetic neuralgia. It is important to note that most of these reported formulations contained water. Thus, unless these formulations were used immediately after their preparation it is very likely significant hydrolysis of the 2-ABAs or their esters removed the acetyl group to give the less potent 2-HBA derivatives. There is the need for non-aqueous or non-alcoholic penetrating excipients in topical 2-ABA and 2-ABA ester formulations for useful shelf life.

Hence, in an embodiment of the invention the components used in the formulations are selected from the following two groups:

Group I: 2-acetyloxy benzoic acid, methyl 2-acetyloxy benzoate, ethyl 2-acetyloxy benzoate, n-propyl 2-actyloxy benzoate, isopropyl 2-acetyloxy benzoate, n-butyl 2-acetyloxy benzoate, isobutyl 2-acetyloxy benzoate.

Group II: d, l and dl isomers of alpha, beta, gamma and delta tocopherols and their acetate esters; d, l and dl isomers of alpha, beta, gamma, and delta cotrienols and their acetate esters; all along with licorice extracts or deglycyrrhized licorice extracts.

Thus, one aspect of this invention involves novel mixtures of compounds selected from group I with compounds selected from group II to give formulations for oral administration having essentially all the beneficial therapeutic properties of 2-ABA but with much less to none of the gastric stress associated with 2-ABA. These novel formulations for ingestion have the general compositions of 350 pts/wt 2-ABA or 400 to 500 pts/wt of 2-ABA esters mixed with 40 to 400 pts/wt tocopherols or their acetates plus 35 to 110 pts/wt tocotrienols or their acetates plus 400 to 1400 pts/wt licorice extract or degglycerrhized licorice extract. A convenient source containing mixture of tocopherols and tocotrienols is either palm seed oil extract (Carotech Inc. among many suppliers) or rice bran oil extract (Eastman Chemicals, among many other suppliers). There is some evidence that the palm seed source is preferred because it has a higher delta tocotrienol content. Theriault et al., 32(5) Clin Biochem 309-19 (1999); Yap et. al., 53(1) J Pharm Pharmacol 67-71 (2001).

An example, but non-limiting, formulation would be: 350 mg 2-ABA (or 400 mg ethyl 2-ABA); 200 mg tocopherol/tocotrienol (palm seed oil extract); and 125 mg licorice extract. Such a formulation might be conveniently contained in a gel capsule with one to eight capsules/day being ingested as needed to alleviate inflammatory conditions throughout the human or animal body.

Another aspect of this invention involves novel sustained release mixtures of 2-ABA or 2-ABA esters with tocopherol or tocopherol acetate for intra-ocular or intra-articular injections as therapies for inflammatory conditions of the eye or joints of animals or humans. The general range of amounts of these components in the formulations is 5 to 95 pts/wt 2-ABA esters or micronized 2-ABA and 95 pts/wt to 5 pts/wt tocopherol or its acetate. An example, but non-limiting, formulation would be: 250 pts/wt ethyl 2-ABA or micronized 2-ABA; 400 pts/wt α-dl or d-tocopherol acetate. This formulation is amenable to injection through 20 gauge to 30 gauge needles in 10 mg to 100 mg aliquots into the vitreous chamber of the eye to provide sustained release of therapeutic levels of 2-ABA or its ester for periods of 10 days to one year. Similarly 10 mg to 3000 mg of these formulations could be injected into the synovial chambers of human or animal joints to provide anti-inflammatory therapy for periods of ten days to one year.

A further aspect of this invention involves novel formulations of 5 pts/wt to 95 pts/wt 2-ABA or its esters with 95 pts/wt to 5 pts/wt tocopherols, tocopherol acetates and/or tocotrienols, tocotrienol acetates for the topical applications to penetrate the skin of humans or animals to alleviate inflammation and pain in the skin or joints. Again, a convenient source of both the tocopherols and tocotrienols would be palm seed oil or rice bran oil extracts. A specific non-limiting formulation would be: 60 pts/wt ethyl 2-ABA or micronized 2-ABA; 40 pts/wt palm seed oil extract.

Without further elaboration, one skilled in the art having the benefit of the preceding description can utilize the present invention to the fullest extent. The following examples are illustrative only and do not limit the remainder of the disclosure in any way.

EXAMPLES

Example 1

Preparation of a Poly(1,3-propanediol carbonate) I from 1,3-propanediol at 65° C. and 96 Hours To 23.6 g (0.2 mole) diethyl carbonate (b.p. 128° C.) was added 15.2 g (0.2 mole) 1,3-propanediol containing 0.05 g (1.25 mmole) of metallic Na to give two liquid phases. These reactants were placed in an open container in a 65° C. oven and were shaken occasionally. After 12 hours, the reactants were a homogeneous solution weighing 38.0 g. The theoretical weight for the loss of 0.4 moles (18.4 g) of ethanol in a complete reaction would be 20.4 g. The heating and occasional shaking were continued to give 27.0 g at 24 hours, 23.2 g at 48 hours, 21.4 g at 72 hours, and 17.4 g at 96 hours. The product oil was washed with 15 ml 5% aqueous acetic acid to two phases. The top phase was the water soluble phase. The 10.5 ml bottom phase was washed with 15 ml water to give 7.5 ml of a poly(1,3-propylene glycol carbonate) oligomer as a water-insoluble oil.

Example 2

Preparation of Poly(1,3-propanediol carbonate) II from 1,3-propanediol at 110-150° C. and 26 Hours A mixture of 76 g (1.0 mole) 1,3-propanediol containing 0.1 g metallic Na (2.5 mmole) and 118 g (1.0 mole) diethyl carbonate was heated at 110° C. As soon as the reactants reached 60° C. they formed a homogeneous solution. After heating 8 hours, the reactants had lost 48 g (52% of theoretical amount of ethanol). The temperature was then raised to 150° C. After 10 hours, the reactants lost another 46 g. A drop of this product completely dissolved in water. The resultant 97 g of oil was mixed with 6 g (0.05 moles) diethyl carbonate and the resultant solution was heated with occasional stirring at 150° C.

After 8 hours, the resultant syrup was found to be partially insoluble in water. The product was washed with 100 ml 5% aqueous acetic acid followed by four washings with 100 ml portions of water to give 46.1 g slightly yellow viscous oil (46.1/102=45% yield).

Example 3

Preparation of a Poly(di-1,2-propylene glycol carbonate) from di-1,2-propylene glycol To 59.0 g (0.5 moles) diethyl carbonate was added 67.0 g (0.5 moles) di-1,2-propylene glycol which had been reacted with 0.02 g Na to form a homogeneous solution. The reactants were placed in an open flask at 100° C. After 12 hours, the solution lost 23.4 g (about 50% of the theoretical 46 g ethanol). After another 15 hours at 150° C. the reactants had lost a total of 53.2 g to give a syrup that was partially insoluble in water. The product was washed with 100 ml 5% aqueous acetic acid followed by four washing with 100 ml portions of water to give 25.2 g colorless viscous, water insoluble liquid poly(di-1,2-propylene glycol carbonate) oligomer.

Example 4

Preparation of a Poly(tri-1,2-propylene glycol carbonate) from tri-1,2-propylene glycol To 0.1 g Na metal was added t 96.0 g (0.5 mole) tri-1,2-propylene glycol. After 5 minutes, the Na had reacted leaving a light yellow oil. 59.0 g (0.5 mole) diethyl carbonate was added to this liquid and the resultant homogeneous solution was heated to 110° C. in an open flask. After 6 hours, the reactants lost 28.0 g (61% of theory). The yellow solution was then heated at 125° C. for 8 hours, whereupon the reactants had lost a total of 48 g (104% of theory). Another 6.0 g (0.5 moles) diethyl carbonate were added and the temperature was raised to 150° C. After 6 hours, the viscous yellow-brown product solution was washed with 100 ml 5% aqueous acetic acid followed by 4 washings with 100 ml portions of water to give 48 g of a viscous orange, water insoluble liquid oligomer.

Example 5

The Assay Procedure for Measuring the Release Profiles of Dexamethasone or Triamcinolone Acetonide from Their Sustained Release Formulations (SRF)

The vials for the release studies were labeled and the weight of each vial was recorded. To each vial was added 3-4 grams of 0.9% saline solution and the weight was recorded. Then the SRF was injected or placed at the bottom of the vial. The weight of the SRF was recorded. An additional amount of 0.9% saline solution was added to a total of 10 grams of saline. The resulting vial was kept in an incubator or water bath at 37° C. Samples were taken periodically to measure the release profile of dexamethasone or triamcinolone acetonide using a HPLC instrument. Sampling protocol was carried out according to the following procedure: Using a disposable pipette, 8 grams of the saline solution containing dexamethasone or triamcinolone acetonide was withdrawn carefully from each vial. 8 grams of 0.9% saline solution was then added to each vial. The vials were kept at 37° C. after sampling.

The HPLC analysis was carried out using a Beckman Gold Instrument with an autosampler. Calibrators with three different concentrations of dexamethasone or triamcinolone acetonide in water were prepared. Calibrators and samples were injected onto a C18 column (Rainin, 250×4.6 mm) containing a guard column (C18, 4.6 mm×1 cm) and analyzed, respectively. The column was eluted using a mobile phase of 45% (or 50%) acetonitrile/water, flow rate 1.0 mL/min, and 7 (or 6) minute run time at an ambient temperature. The detector wavelength of 238 nm was used. The dexamethasone or triamcinolone acetonide (retention times, 6-4 minutes) concentration of each sample was calculated from the standard curve using the software of the Beckman Gold instrument.

A wash program to clean the HPLC column was set up during the HPLC run. After every three or four injections, a sample containing 20 μL of acetonitrile was injected onto the column, the column was eluted with a mobile phase of 99% acetonitrile/water, flow rate 1 mL/min, and a run time 7 minutes. Then the column was equilibrated back to the original mobile phase by injecting 20 μL of acetonitrile, eluting with 45% (or 50%) acetonitrile/water, flow rate 1 mL/min, and a run time 7 minutes.

The sampling times and the active ingredient (for example dexamethasone or triamcinolone acetonide) concentrations determined from HPLC were recorded and tabulated. The percent drug released and the amount of drug released were each calculated from a Microsoft Excel software program.

Example 6

Preparation of Mixtures of Dexamethasone in poly(1,3-propanediol carbonate) I and Their Release Profiles Preparation of 10% dexamethasone in poly(1,3-propanediol carbonate) I: One portion by weight of dexamethasone was mixed with nine portions by weight of the poly(1,3-propanediol carbonate) I prepared in Example 1. The resulting suspension was stirred at an ambient temperature until a homogeneous mixture formed. The mixture was then aliquoted and analyzed for the release profile as shown in FIG. 1.

Preparation of 20% dexamethasone in poly(1,3-propanediol carbonate) I: Two portions by weight of dexamethasone were mixed with eight portions by weight of the poly(1,3-propanediol carbonate) I prepared in Example 1. The resulting suspension was stirred at an ambient temperature until a homogeneous mixture formed. The mixture was then aliquoted and analyzed for the release profile as shown in FIG. 1.

Example 7

Figure 2:
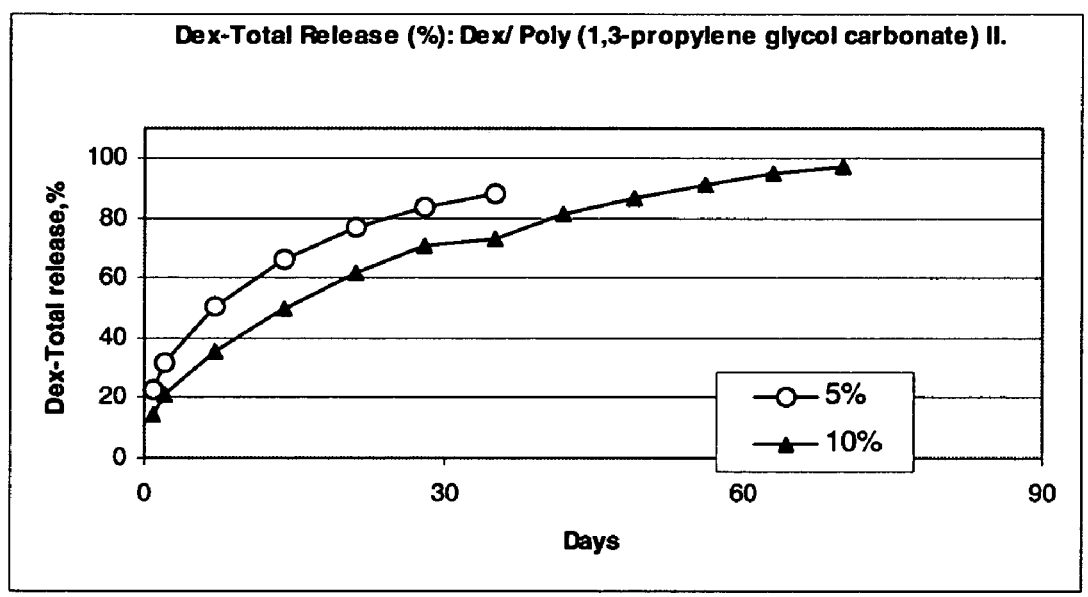
FIG. 2 presents dissolution profiles of Dex from two formulations of Dex/poly(1,3-propanediol carbonate)II.

Preparation of Mixtures of Dexamethasone in poly(1,3-propanediol carbonate) II and Their Release Profiles Preparation of 5% dexamethasone in poly(1,3-propanediol carbonate) II: One portion by weight of dexamethasone was mixed with nineteen portions by weight of the poly(1,3-propanediol carbonate) II prepared in Example 2. The resulting suspension was stirred at an ambient temperature until a homogeneous mixture formed. The mixture was then aliquoted and analyzed for the release profile as shown in FIG. 2.

Preparation of 10% dexamethasone in poly(1,3-propanediol carbonate) II: One portion by weight of dexamethasone was mixed with nine portions by weight of the poly(1,3-propanediol carbonate) II prepared in Example 2. The resulting suspension was stirred at an ambient temperature until a homogeneous mixture formed. The mixture was then aliquoted and analyzed for the release profile as shown in FIG. 2.

Example 8

Figure 3:
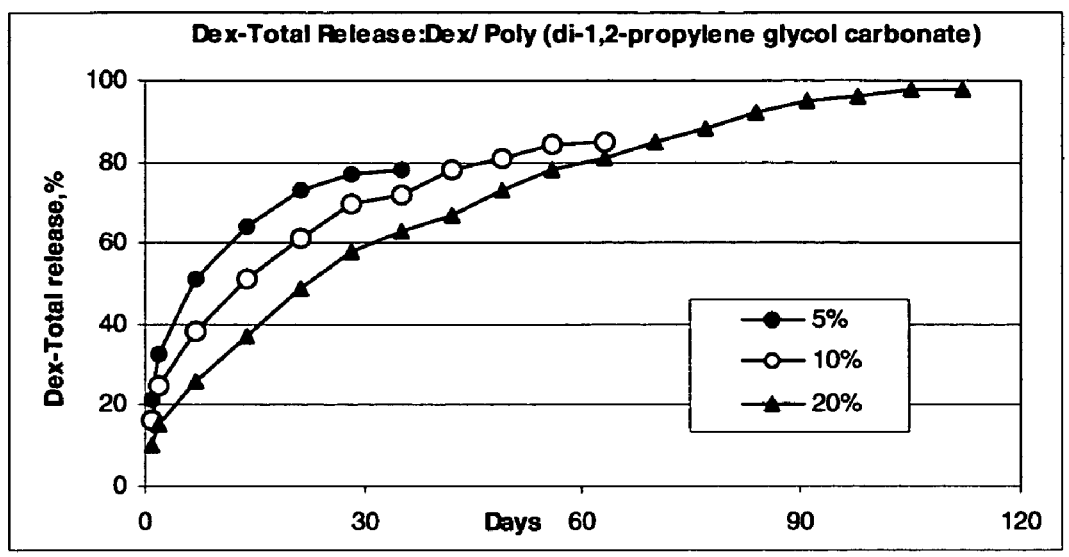
FIG. 3 represents dissolution profiles of Dex from three formulations of Dex/poly(di-1,2 propylene glycol carbonate).

Preparation of Mixtures of dexamethasone in poly(di-1,2-propylene glycol carbonate) and Their Release Profiles Preparation of 5% dexamethasone in poly(di-1,2-propylene glycol carbonate): One portion by weight of dexamethasone was mixed with nineteen portions by weight of the poly(di-1,2-propylene glycol carbonate) prepared in Example 3. The resulting suspension was stirred at an ambient temperature until a homogeneous mixture formed. The mixture was then aliquoted and analyzed for the release profile as shown in FIG. 3.

Preparation of 10% dexamethasone in poly(di-1,2-propylene carbonate): One portion by weight of dexamethasone was mixed with nine portions by weight of the poly(di-1,2-propylene glycol carbonate) prepared in Example 3. The resulting suspension was stirred at an ambient temperature until a homogeneous mixture formed. The mixture was then aliquoted and analyzed for the release profile as shown in FIG. 3.

Preparation of 20% dexamethasone in poly(di-1,2-propylene glycol carbonate): Two portions by weight of dexamethasone were mixed with eight portions by weight of the poly(di-1,2-propylene glycol carbonate) prepared in Example 3. The resulting suspension was stirred at an ambient temperature until a homogeneous mixture formed. The mixture was then aliquoted and analyzed for the release profile as shown in FIG. 3.

Example 9

Figure 4:
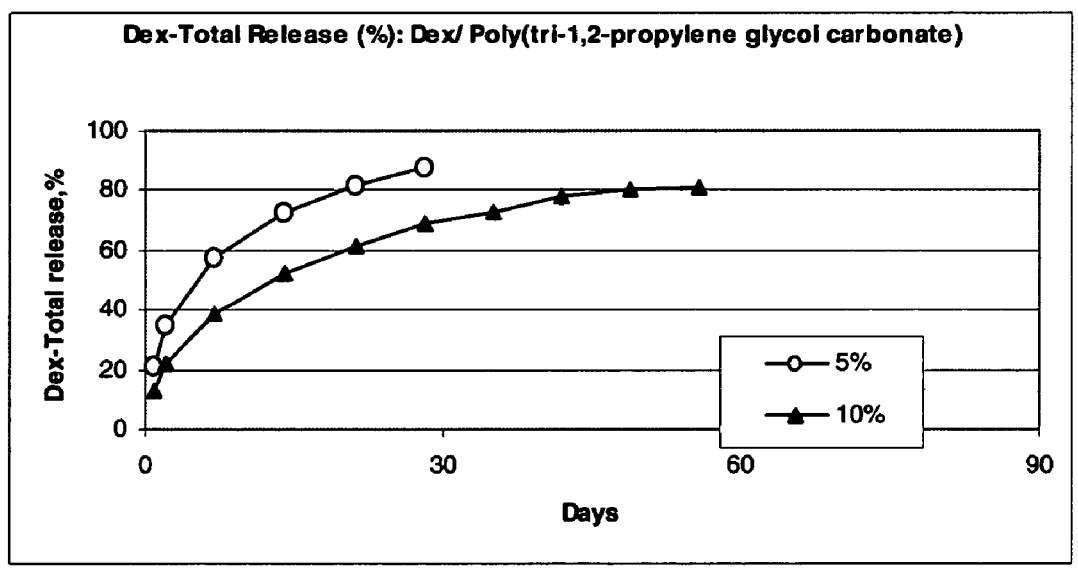
FIG. 4 depicts dissolution profiles of Dex from two formulations of Dex/poly(tri-1,2 propylene glycol carbonate).

Preparation of Mixtures of Dexamethasone in poly(tri-1,2-propylene Glycol Carbonate) and Their Release Profiles Preparation of 5% dexamethasone in poly(tri-1,2-propylene glycol carbonate): One portion by weight of dexamethasone was mixed with nineteen portions by weight of the poly(tri-1,2-propyleneglycol carbonate) prepared in Example 4. The resulting suspension was stirred at an ambient temperature until a homogeneous mixture formed. The mixture was then aliquoted and analyzed for the release profile as shown in FIG. 4.

Preparation of 10% dexamethasone in poly(tri-1,2-propylene glycol carbonate): One portion by weight of dexamethasone was mixed with nine portions by weight of the poly(tri-1,2-propylene glycol) carbonate prepared in Example 4. The resulting suspension was stirred at an ambient temperature until the formation of a homogeneous mixture. The mixture was then aliquoted and analyzed for release profile as shown in FIG. 4.

Example 10

Figure 5:
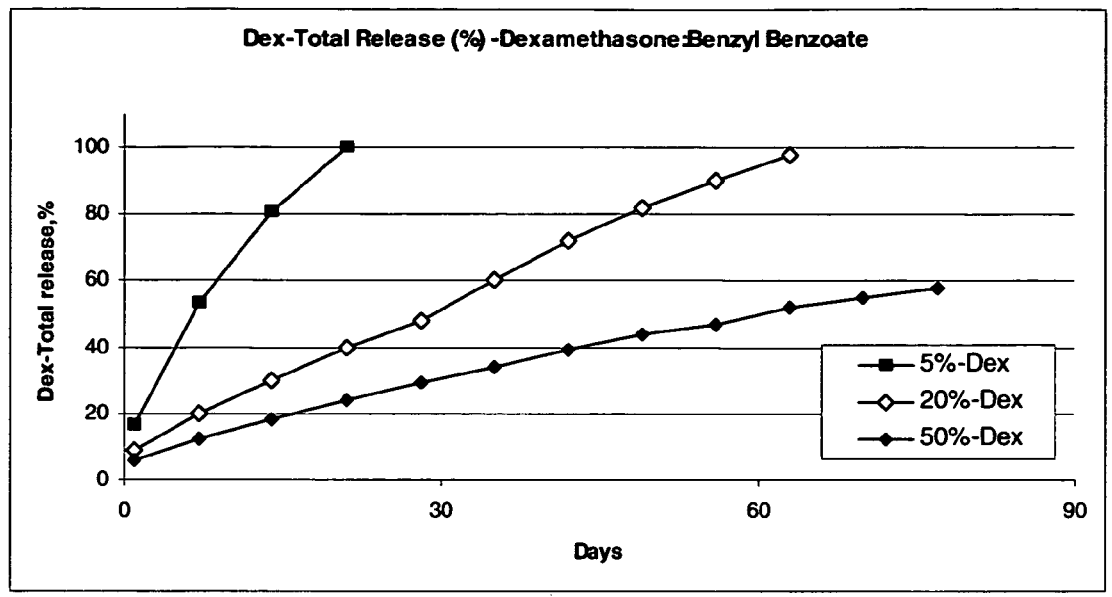
FIG. 5 depicts dissolution profiles of Dex released from three formulations of Dex/benzyl benzoate.

Preparation of Mixtures of Dexamethasone in Benzyl Benzoate and Their Release Profiles In preparing 20% dexamethasone in benzyl benzoate, two portions by weight of dexamthasone was mixed with eight portions by weight of benzyl benzoate. The resulting suspension was stirred at an ambient temperature until a homogeneous mixture formed. The mixture was then aliquoted and analyzed for the release profile as shown in FIG. 5.

Formulations containing 5% and 50% dexamethasone in benzyl benzoate were prepared under similar conditions to the 20% formulation, with the exception of the weight ratio of dexamethasone/benzyl benzoate. Mixtures of 5% and 50% dexamethasone in benzyl benzoate were prepared, and the resulting mixtures were aliquoted and small portions were analyzed for the release profiles as shown in FIG. 5.

Dexamethasone in benzyl benzoate forms a uniform suspension. A formulation of 25% is easily syringeable. As the suspension is slowly injected into the eye's posterior segment, a uniform spherical deposit (reservoir) is formed in the vitreous body. Dexamethasone is then released slowly into the vitreous humor of the posterior segment. Dexamethasone and benzyl benzoate are eventually metabolized to byproducts to be excreted in the urine.

Example 12

Figure 6:
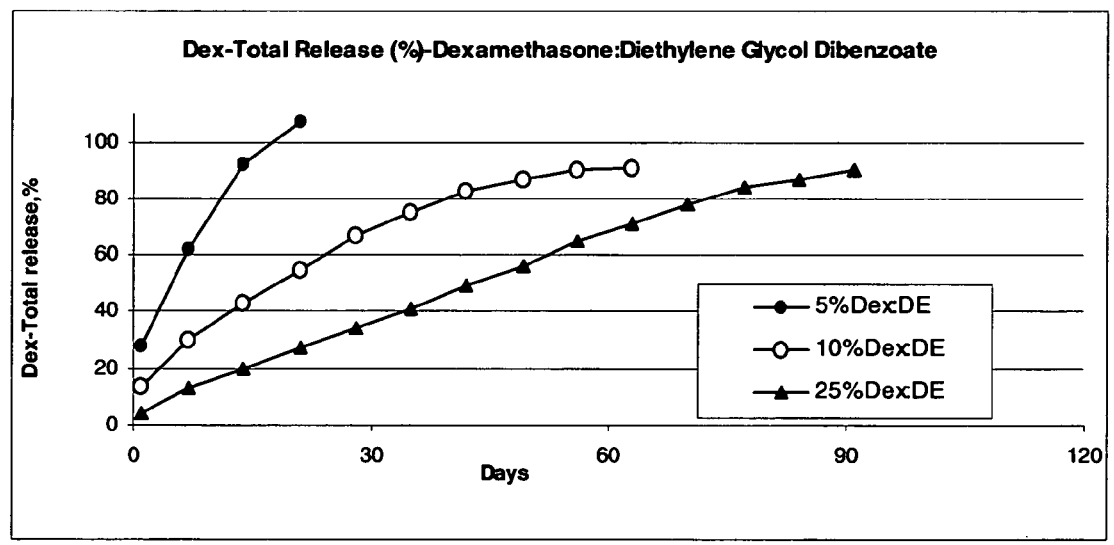
FIG. 6 depicts dissolution profiles of Dex released from three formulations of Dex/diethylene glycol dibenzoate.

Preparation of Mixtures of Dexamethasone in Diethylene Glycol Dibenzoate and Their Release Profiles Ten percent dexamethasone in diethylene glycol dibenzoate was prepared by mixing one portion by weight of dexamethosone (Dex) with nine portions by weight of diethylene glycol dibenzoate. The resulting suspension was stirred at an ambient temperature until a homogeneous mixture formed. The mixture was then aliquoted and analyzed for the release profile as shown in FIG. 6.

Using conditions similar to that of the 10% Dex/diethylene glycol dibenzoate preparation, with the exception of the weight ratios, mixtures of 5% and 25% Dex/diethylene glycol dibenzoate formulations were prepared. The resulting mixtures were aliquoted and small portions analyzed for the release profiles as described previously. The resulting release profiles are shown in FIG. 6.

Example 13

Figure 7:
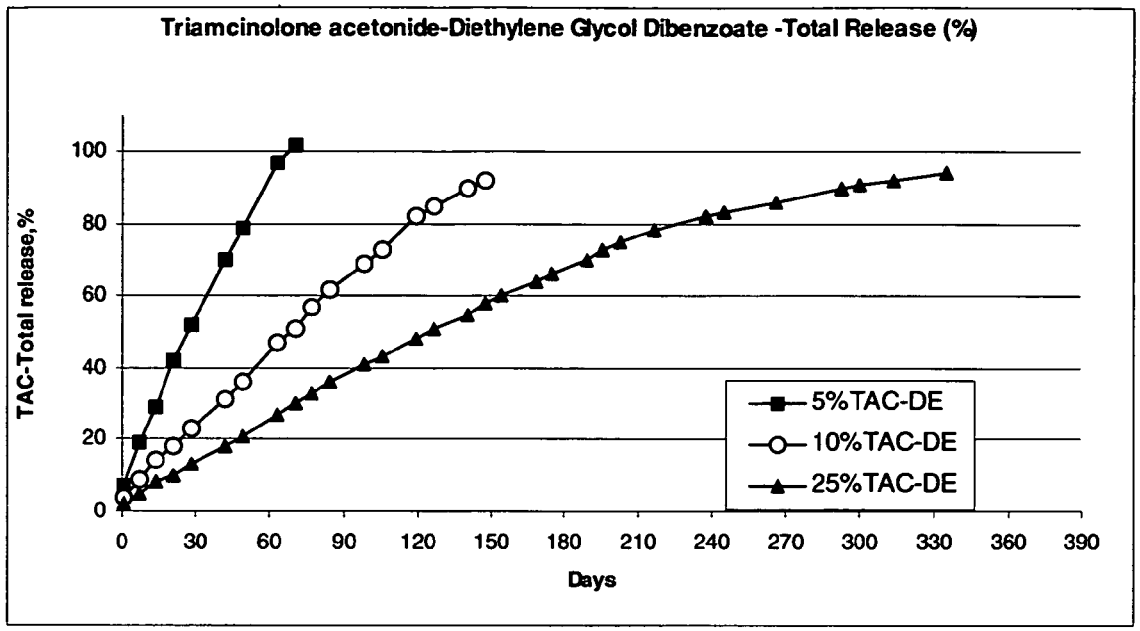
FIG. 7 depicts dissolution profiles of triamcinolone acetonide released from three formulations of triamcinolone acetonide/diethylene glycol dibenzoate.

Preparation of mixtures of Triamcinolone Acetonide in Diethylene Glycol Dibenzoate and Their Release Profiles Preparations of 5%, 10% and 25% triamcinolone acetonide in diethylene glycol dibenzoate were prepared as follows: a 0.5, 1.0, or 2.5 portion by weight of triamcinolone acetonide was mixed with a 9.5, 9.0 or 7.5 portion by weight, respectively, of diethylene glycol dibenzoate. The resulting suspension was stirred at an ambient temperature until a homogeneous mixture formed. The mixture was then aliquoted and analyzed for the release profile as described previously. The resulting release profiles are shown in FIG. 7.

Example 14

Figure 8:
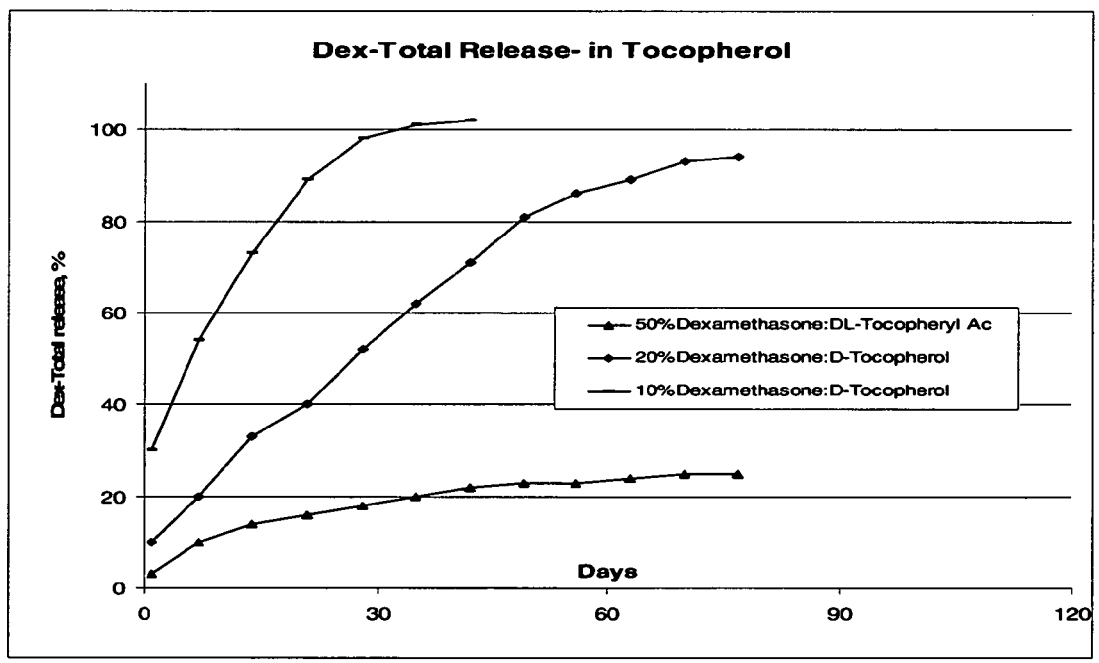
FIG. 8 depicts dissolution profiles of Dex released from three formulations of Dex/d-tocopherol, and dl-tocopheryl acetate.

Preparation of Mixtures of Dexamethasone in d-tocopherol or d,l-tocopherol Acetate and Their Release Profiles For the preparation of 10% Dex in d-tocopherol, one portion by weight of Dex was mixed with nine portions by weight of d-tocopherol. The resulting suspension was stirred at an ambient temperature until a homologous mixture formed. The mixture was then aliquoted and analyzed for release profile as shown in FIG. 8.

For the preparation of 20% Dex in d-tocopherol, two portions by weight of Dex was mixed with eight portions by weight of d-tocopherol. The resulting suspension was stirred at an ambient temperature until the formation of a homologous mixture. The mixture was then aliquoted and analyzed for release profile as shown in FIG. 8.

For the preparation of 50% Dex in dl-tocopherol acetate, five portions by weight of Dex were mixed with five portions by weight of dl-tocopherol acetate. The resulting suspension was stirred at ambient temperature until a homologous mixture formed. The mixture was then aliquoted and analyzed for the release profile as shown in FIG. 8.

Example 15

Figure 9:
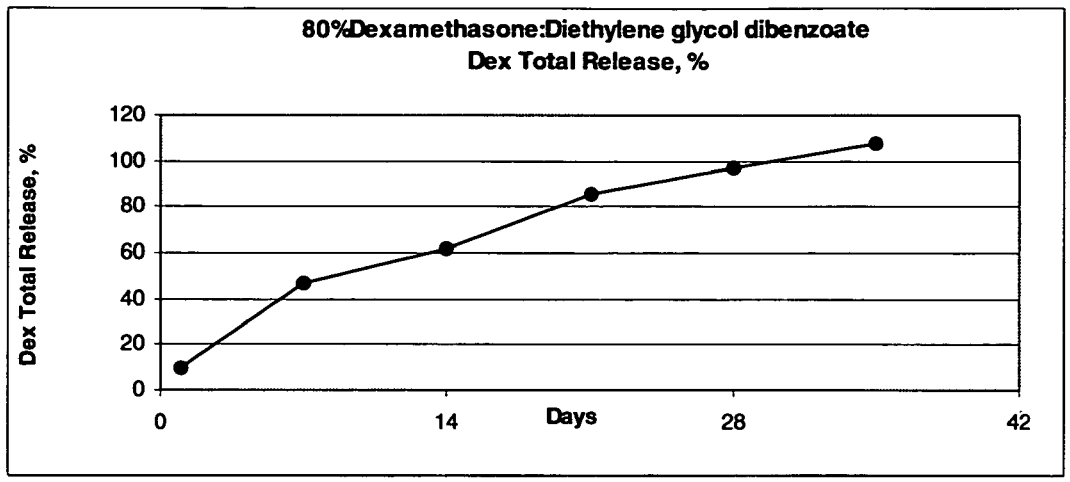
FIG. 9 depicts a dissolution profile of Dex released from a Dex/diethylene glycol dibenzoate formulation.

Manufacturing of a Solid Drug Delivery System with Dexamethasone and Diethylene Glycol Dibenzoate and Its Release Profile Dexamethasone powder and diethylene glycol dibenzoate by weight were mixed thoroughly by mortar and pestle. The mixture was placed into a Parr pellet press of 2 mm diameter to form a solid pellet at 25° C. suitable for an implant. The newly formed pellet was then weighed in a microbalance before testing for in vitro kinetics as shown in FIG. 9.

Example 16

Figure 10:
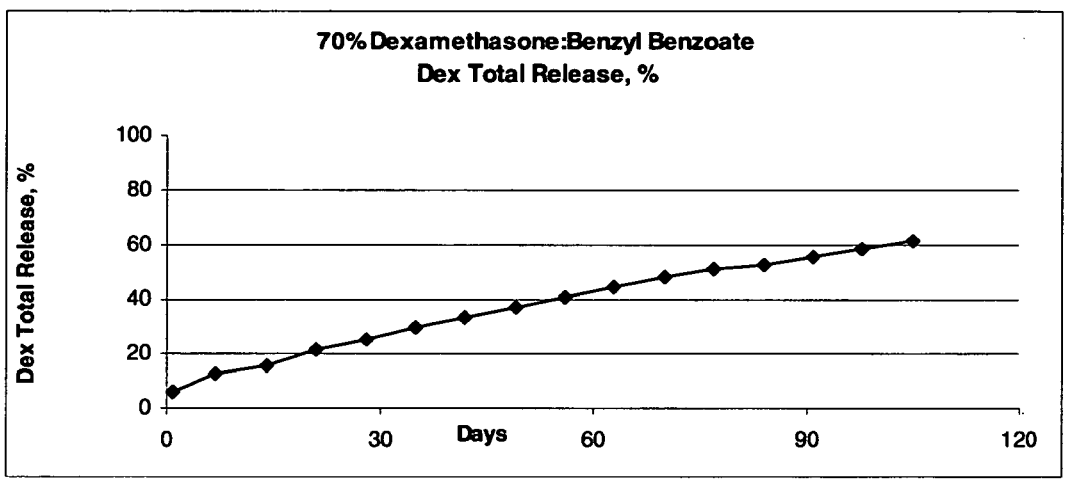
FIG. 10 depicts a dissolution profile of Dex released from a Dex/benzyl benzoate formulation.

Manufacturing of a Solid Drug Delivery System with Dexamethasone and Benzyl Benzoate and Its Release Profile Dexamethasone powder and benzyl benzoate by weight were mixed thoroughly by mortar and pestle. The mixture was then placed into a 2 mm diameter Parr pellet press to form a pellet at 25° C. suitable for an implant. The formed pellet was weighed and recorded in a microbalance before testing for in vitro kinetics as shown in FIG. 10.

Example 17

Figure 11:
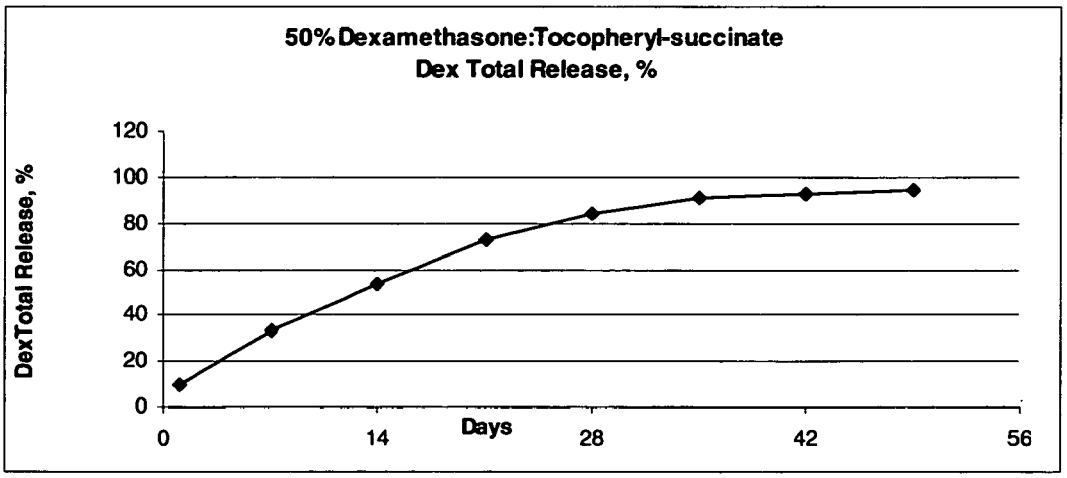
FIG. 11 depicts a dissolution profile of Dex released from a Dex/tocopheryl succinate formulation.

Manufacturing of a Solid Drug Delivery System with Dexamethasone and Tocopheryl Succinate and Its Release Profile Dexamethasone powder and tocopheryl succinate powder were thoroughly mixed at a ratio of 50/50 by weight. The well-mixed powder was filled into a single barrel extruder and heated for 1 hour at 65° C. before extruding through a 1 mm orifice. Micropellets of varying sizes suitable for implants were cut from the extruded filaments for in vitro kinetic testing as shown in FIG. 11.

Example 18

Combination Formulations

Figure 12A:
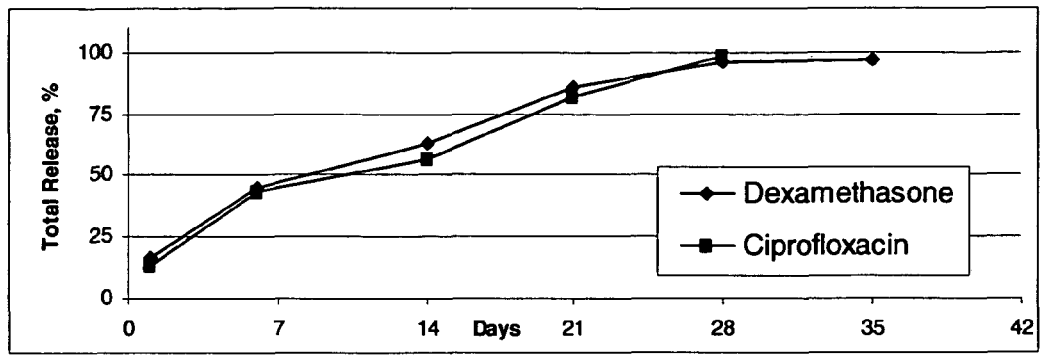
FIG. 12 depicts a dissolution profile of Dex and Ciprofloxacin from a 1:1 formulation of those components in benzyl benzoate (Panel A) and a 3:1 formulation of Dex and Ciprofloxacin in benzyl benzoate (Panel B).

Combination with two or more drugs conveniently formulated with an excipient such as benzyl benzoate provides for sustained and controlled release of the active agents. The variables of volume, concentration and percentages of the ingredients are factors influencing duration and therapeutic concentration of the drug(s) released. As an example, in a 20% (wt) formulation of a 1:1 dexamethasone:ciprofloxacin in benzyl benzoate, the release profile of the two drug is similar and the duration is about twenty-eight to thirty-five days. The release profile of the two drugs is shown in FIG. 12A.

Figure 12B:
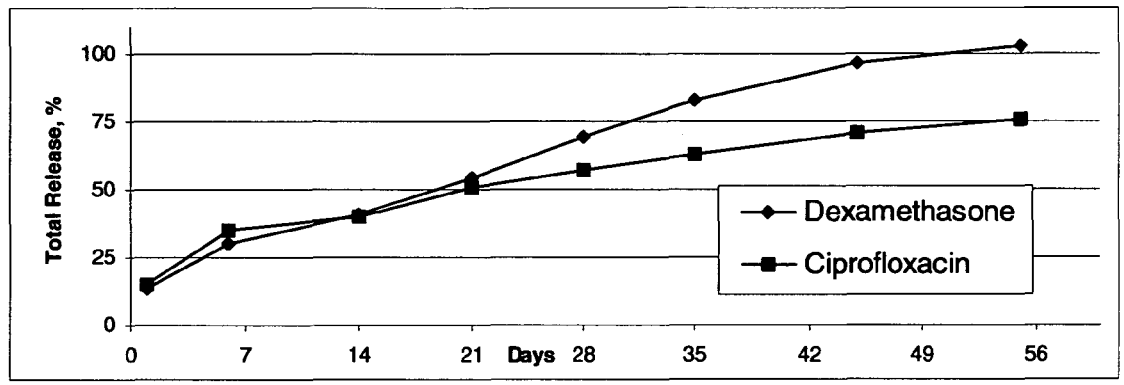

Another useful composition comprises dexamethasone and ciproloxin at a ratio of 3:1 dexamethasone:ciprofloxin. The duration of release of each drug is prolonged significantly, to about sixty days for dexamethasone and longer for ciprofloxin, as shown in FIG. 12B.

Example 19

Pharmacokinetics and Metabolism of Injected Formulation Comprising Dex

To examine the in vivo release of dexamethasone in vivo, a composition of 25% dexamethasone by weight in benzyl benzoate (DB) was used: 25 µl (low dose) contained 6 mg dexamethasone, 50 µl (high dose) contained 12 mg dexamethasone. Benzyl benzoate served as placebo.

The in vivo release of the DB composition was studied in twenty-four rabbits. Twenty-five µl of 25% DB was injected into the posterior segment of one eye of twelve animals and the contralateral eye received a placebo. Another twelve animals received 50 µl of the DB in one eye and 50 µl of the BB placebo in the second eye. Animals were euthanized at the appropiate time points and vitreous humor samples were removed surgically. Dexamethasone concentration was determined by high pressure liquid chromatography (HPLC) as described in Example 5.

Figure 13:
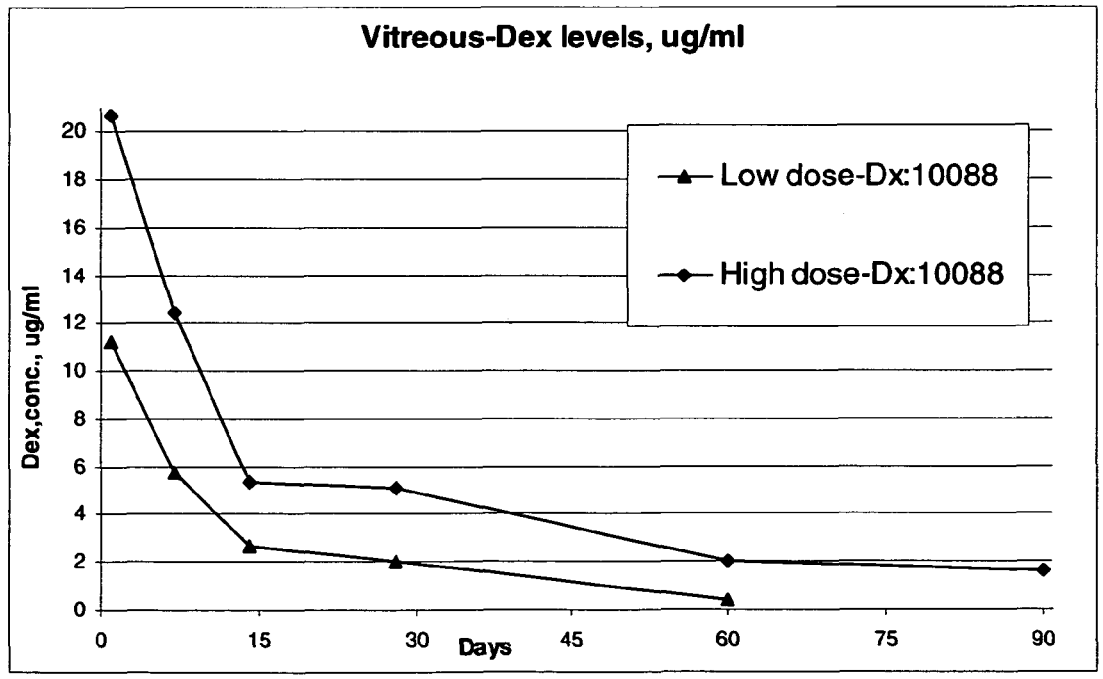
FIG. 13 depicts the concentration of Dex released into the vitreous humor from two formulation of Dex in benzyl benzoate.

For the high dose, the concentration of released dexamethasone was maximal during the first week after insertion, with a mean of 5.56 µg/ml from Day 7 to Day 90, declining to a mean level of 1.85 µg/ml by Day 90. With the low dose, the mean level of dexamethason was 2.8 µg/ml from Day 7 to Day 60, declining to a mean level of 0.8 µg/ml. FIG. 13. Dexamethasone was not detected in any of the control eyes.

Clinically, the 24 animals receiving the placebo or low or high doses of the DB showed no evidence of inflammation or infection for the entire study. Animals were examined twice weekly both by slit-lamp ophthalmoscopy and fundoscopic examination. No evidence of cataracts, vitreous, or retinal abnormality was observed.

Figure 14:
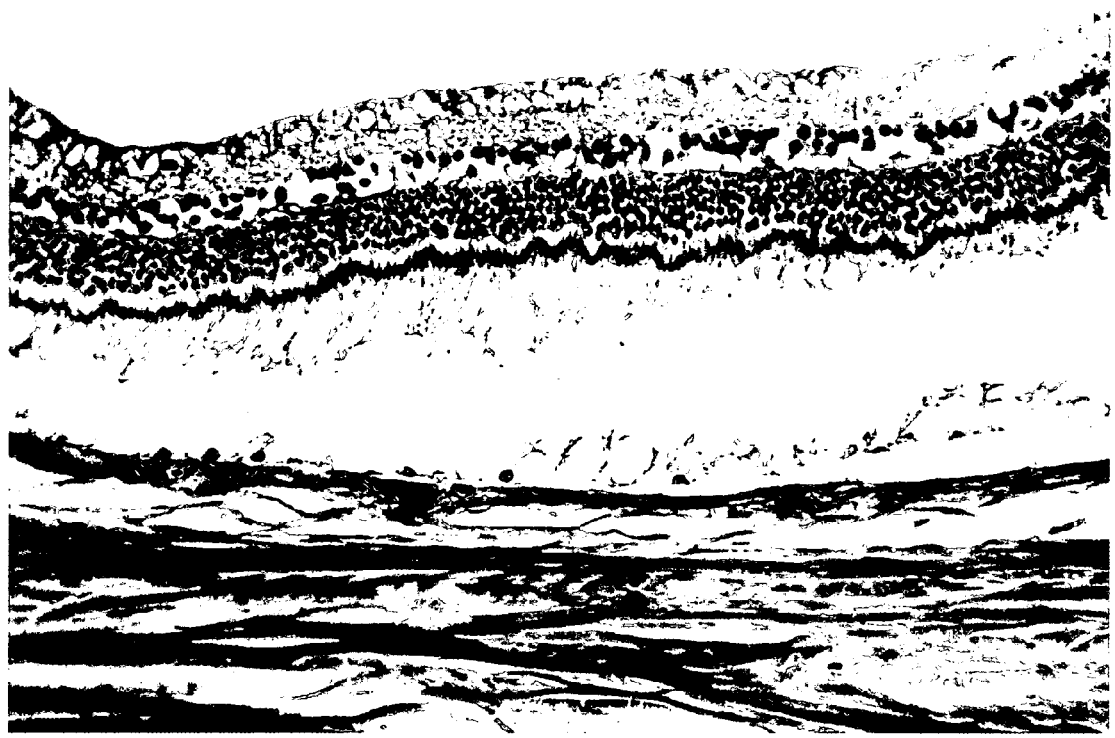
FIG. 14 represents a histopathological slide of rabbit eye tissue thirty days after a posterior segment injection of a formulation of 25% Dex in benzyl benzoate.

Regarding histopathology, three animals were injected with 25 µl of the DB in one eye and 25 µl of the placebo (BB) in the contralateral eye. Another three animals were injected with 50 µl DB in one eye and 501 µl BB in the other eye. They were followed clinically weekly and were sacrificed for histopatholoy at 30 days for the low dose and at 90 days for the high dose. Eyes were fixed in 10% buffered formalin and examined after H & E staining. The anterior segment comprising the cornea, anterior chamber, iris, ciliary body, and lens were normal. The pigment epithelium, Bruch's membrane, and the choroids were all within normal limits. See FIG. 14. There were no obvious differences in the histopathology between the treated and control eyes.

To further examine the in vivo anti-inflammatory effect of DB, 25 µl of 25% DB was injected into the vitreous of one eye of three New Zealand White (NZW) rabbits weighing 3 kg-3.5 kg. Twenty-four hours later, 2.5 mg of bovine serum albumin (BSA) was injected into both eyes. The animals were examined daily as well as ophthalmologically. Between 10 to 14 days, uveitis with severe fibrinous reaction occurred in the eye unprotected by DB. In the eyes injected with DB, little to no inflammation was detected on examination. Histopathology, the unprotected eye showed chronic and acute inflammatory cells in the uveal tissues as well as in the anterior chamber and the vitreous cavity. In the protected eye, there was minimal evidence of inflammation with few round cell infiltration in the choroids. The cornea, iris, retina and the choroids were histologically intact. See Table 1 below.

TABLE 1

Inflammation in NZW

| NZW | Day 0 | Day 14 |
|---|---|---|
| 1 | | |
| OD | BSA/DB* | 3+ |
| OS | BSA | 0-1+ |
| 2 | | |
| OD | BSA | 3-4+ |
| OS | BSA/DB | Trace |
| 3 | | |
| OD | BSA/DB | 0 |
| OS | BSA | 4+ |

BSA: bovine serum albumin;
DB: 25% dexamethasone/benzylbenzoate
OD: right eye,
OS: left eye;
0-4: severity of posterior segment inflammation, 4+ being maximum Another three NZW rabbits were immunized intravenously (IV) with 10 mg of BSA. Twenty-one days later, following intradermal injection of 0.5 mg BSA/0.1 ml saline, all animals demonstrated a strong (+4) Arthus reaction indicating the animals were systemically immuned to the BSA. On day thirty, one eye of each animal was injected intravitreally with 25 µl of a 25% DB composition, and 24 hours later 0.5 mg BSA/0.1 ml normal saline was injected into both eyes. Severe uveitis developed and persisted in the ensuing seven to ten days in the unprotected eye, while the protected eye was judged to be normal. On day sixty, repeat skin testing showed that the (+4) Arthus reaction remained intact, and reinjection of 0.5 mg BSA/0.1 ml normal saline showed similar protection as observed on day 30. These studies imply that DB has immediate and sustained protective effect in the experimental eye. When these animals were again challenged with 0.5 mg BSA/0.1 ml normal saline at 90 days, uveitis developed in all eyes, but the inflammation in the protected (DB) eye appeared to be less severe. See Table 2 below. Protection against inflammation with 25 µl of DB lasted for sixty days. At ninety days, there may have been an insufficient therapeutic level of Dexamethasone in the eye.

TABLE 2

Inflammation in protected and unprotected NZW eyes.

| NZW | Day 0 | Day 14 | Day 30 | Day 60 | Day 90 |
|---|---|---|---|---|---|
| 1 | | | | | |
| OD | BSA | | 3-4+ | 3-4+ | 3-4+ |
| OS | BSA/DB* | | 0 | 0 | 2-3+ |
| 2 | | | | | |
| OD | BSA | | 4+ | 3-4+ | 3+ |
| OS | BSA/DB | | Trace | 0+ | 2-3+ |
| 3 | | | | | |
| OD | BSA | | 4+ | 4+ | 4+ |
| OS | BSA/DB | | 0-1+ | 0 | 2-4+ |

BSA: bovine serum albumin;
DB: 25% dexamethasone/benzylbenzoate
OD: right eye,
OS: left eye;
0-4: severity of posterior segment inflammation, 4+ being maximum Another three NZW rabbits were immunized similarly IV with 10 mg BSA. Twenty-four hours later, one eye of each animal was injected with 50 µl of 25% DB. At three months (90 days), intradermal skin testing evoked a +4 reaction. One week later, 0.5 mg BSA/0.1 ml normal saline was injected in both eyes of each animal. The protected eye (injected with 50 µl 25% DB) showed little to no clinical uveitis when compared to the contralateral unprotected eye. This indicates that chronic sustained release of Dexamethasone was able to protect the eye up to three months when challenged locally with BSA. See Table 3 below.

TABLE 3

Sustained protection in protected NZW eyes.

| NZW | Day 0 | Day 90 |
|---|---|---|
| 1 | | |
| OD | BSA/DB* | 0-1+ |
| OS | BSA | 4+ |
| 2 | | |
| OD | BSA/DB | 0+ |
| OS | BSA | 3-4+ |
| 3 | | |
| OD | BSA/DB | 0-1+ |
| OS | BSA | 4+ |

BSA: bovine serum albumin;
DB: 25% dexamethasone/benzylbenzoate
OD: right eye,
OS: left eye;
0-4: severity of posterior segment inflammation, 4+ being maximum Example 20

Pharmacokinetics and Metabolism of Injected Formulation Comprising TA

A composition of 25% TA (Triamcinolone Acetonide) by weight in benzyl benzoate (TA/B) was used: 25 µl containing 7.0 mg TA and 50 µl containing 14 mg TA. Benzyl benzoate (BB) served as placebo.

Figure 15:
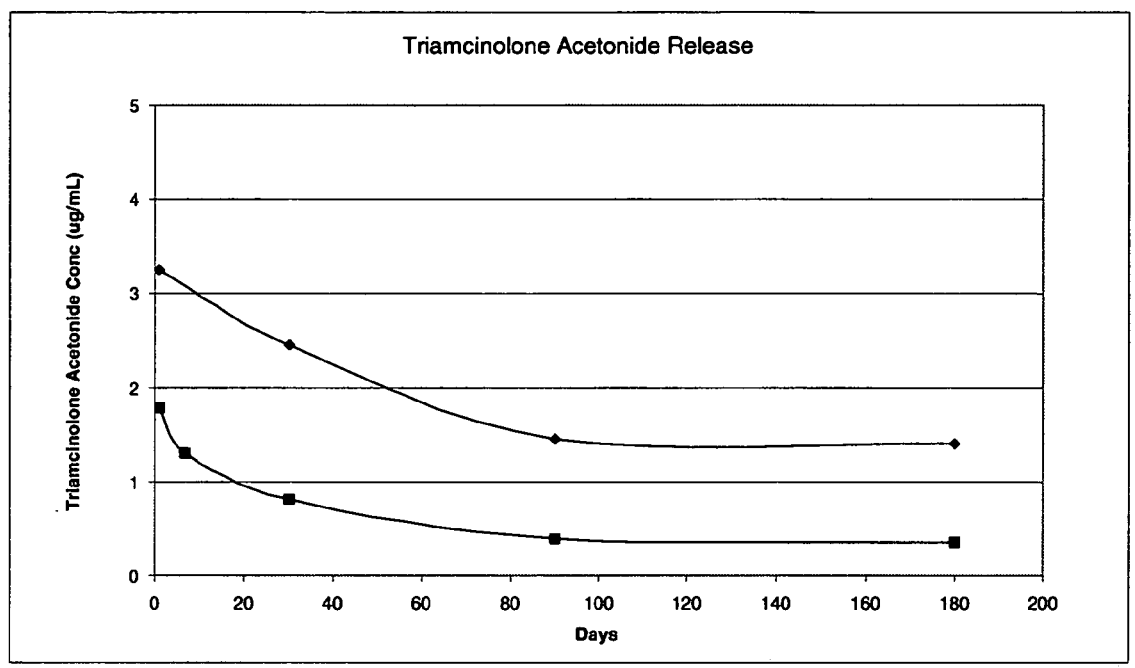
FIG. 15 depicts the vitreous concentration of tramcinolone acetonide (TA) released from a TA benzyl benzoate composition.

The in vivo release of the TA was studied in twenty-seven rabbits. Twenty-five µl (25 µl) of the composition was injected into the posterior segment of one eye of twelve animals and the contralateral eye received 25 µl of BB. Another twelve animals received 50 µl of the same composition into posterior segment of one eye and 50 µl BB into the second eye. Animals were euthanized at the appropriate time points (each time point n=3) and vitreous humor samples were removed surgically for TA concentration by high-pressure liquid chromatography (HPLC) as described in Example 5. The mean vitreous concentration TA for the 50 µl TA/B at twenty-four hours was 3.25 µg/ml; at 1 month 2.45 µg/ml; at three months 1.45 µg/ml; and at six months 1.56 µg/ml. The mean vitreous TA level over the 6 month period was 2.17 µg/ml. The mean vitreous concentration of TA of the 25 µl TA/B animals was 1.78 µg/ml at twenty-four hours; 1.31 µg/ml at one week; 0.81 µg/ml at one month; 0.4 µg/ml at three months; and 0.36 µg/ml at six months, with a mean of 0.93 µg/ml over a six month period. TA was not detected in any of the control eyes. See FIG. 15. For the 25 µl dose, near zero-order release was been observed in vivo for 270 days (data not shown). For the 50 µl dose, near zero-order release has been observed in vivo for 365 days (data not shown).

Clinically, the twenty-seven animals receiving the BB placebo showed no evidence of inflammation or infection for the entire study. Animals were examined twice weekly both by slit-lamp ophthalmoscopy and fundoscopic examination. No evidence of cataracts, vitreous or retinal abnormality was seen.

Regarding histopathology, six animals were injected with 50 µl of 25% TA/B in the right eye and 50 µl of BB in the other eye. They were followed clinically weekly and were sacrificed for histopathology at 180 days. Eyes were fixed in 10% buffered formalin and examined after H & E staining. The anterior segment comprising the cornea, anterior chamber, iris, ciliary body and lens was normal. Histopathology of the posterior segment (including the vitreous, retina, photoreceptors cells, pigment epithelium, Bruch's membrane and the choroids) was within normal limits. There were no obvious differences in the histopathology between the treated and the control eyes.

Example 21

Solid Implant Comprising Dex

Figure 16:
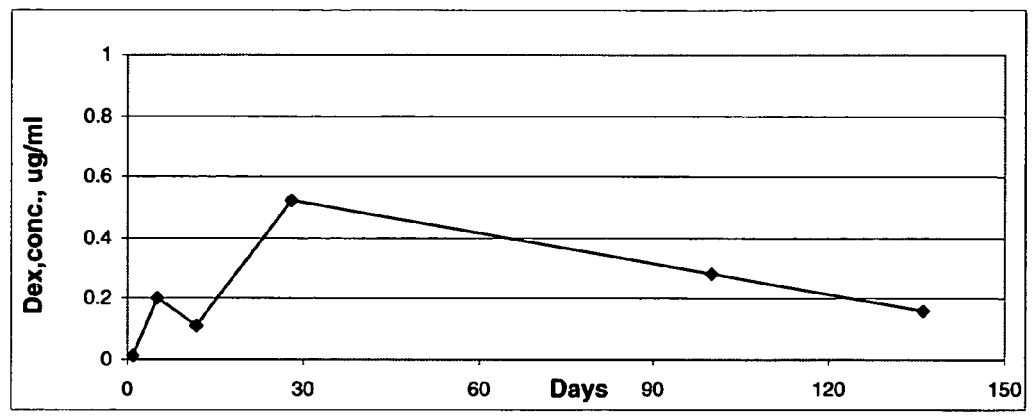
FIG. 16 depicts the in vivo release of Dex released into the aqueous humor from a Dex/dl-alpha tocopherol succinate formulation.

The levels of dexamethasone released from a solid implant was studied in the anterior chamber of a NZW rabbit. A mixture of 50:50 dexamethasone (Upjohn) and dl-alpha tocopherol succinate (Sigma) was extruded through an aperature of 790 uM mm at 25° C. One (1) mgm of this extruded mixture was surgically placed in the right anterior chamber of a 4 kg NZW female rabbit. Sampling of the aqueous humor from the anterior chamber (AC) for HPLC dexamethasone analysis was performed in accordance with the above example. Therapeutic sustained release levels of dexamethasone were observed. See FIG. 16. Clinically, the animal's eye was completely quiescent and the composition was judged to be biocompatible.

Example 22

Figure 17:
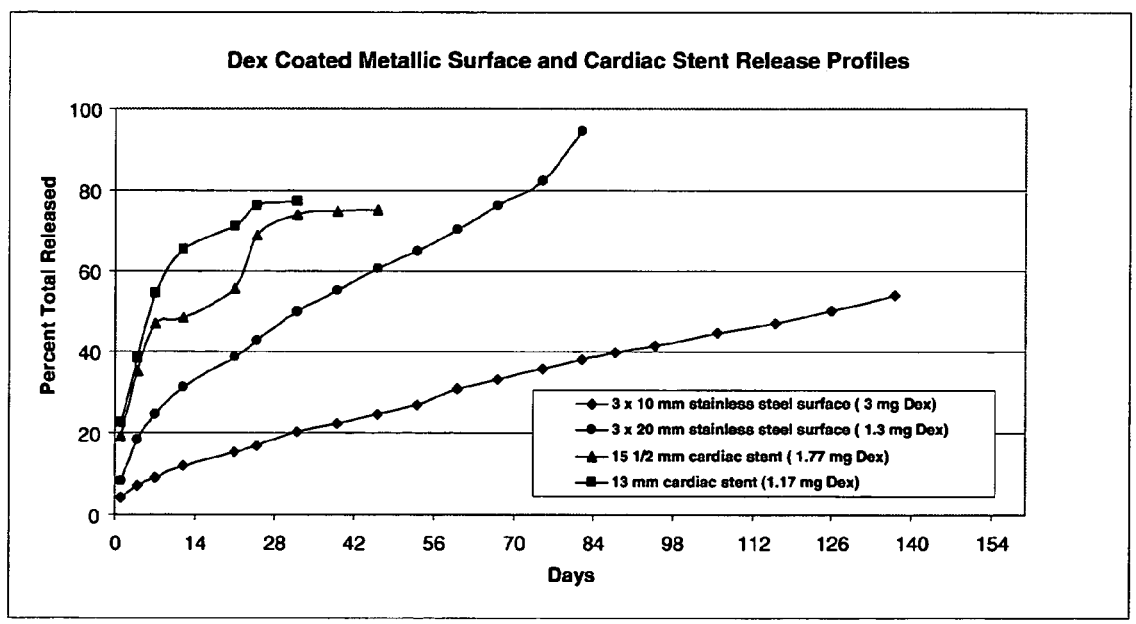
FIG. 17 depicts the dissolution of Dex from a Dex/acetone/tocopherol succinate formulation applied to solid surfaces.

Sustained Release of Dexamethasone/dl-alpha Tocopherol Succinate Coating of Stainless Steel Surface and Cardiac Stents A mixture of 2:8:1 (wt) of dexamethasone:acetone:tocopherol succinate coating was applied to two stainless steel tubing surfaces and two commercial cardiac stents. Coating was achieved by dipping and oven drying. Elution of dexamethasone for HPLC analysis was done in a 20 ml distilled water vial and exchange of 75% of the total volume took place per period of assay. See FIG. 17. Tocopherol succinate has been demonstrated to be an effective coating medium on steel surfaces for controlled drug release. The application of this methodology could be extended to various materials and surfaces including wood, glass, various metals, rubber, synthetic surfaces such as teflon, plastics, polyethylene tubings and the like.

Example 23

Formulations Comprising Cyclosporine in Tocopherol Succinate

Figure 18:
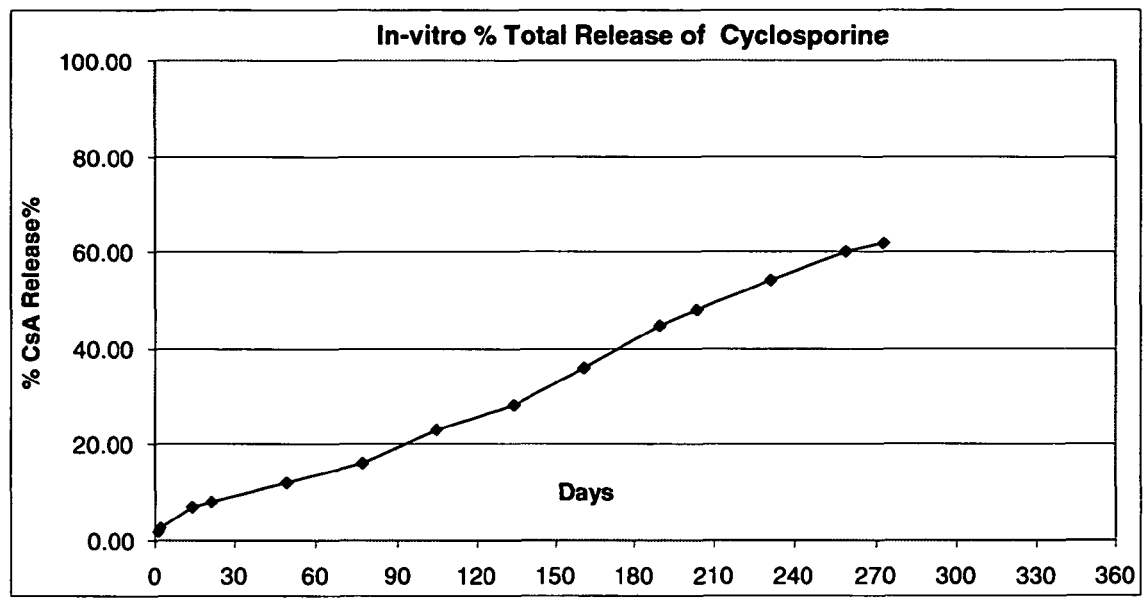
FIG. 18 shows the dissolution profile of cyclosporin from a cyclosporine/tocopherol succinate formulation.

To study the in vitro release of 25:75 dl-alpha tocopherol:Cyclosporin A, cyclosporin was mixed with tocopherol succinate and extruded at 25° C. through an aperature of 790 µM. One mg (1 mg) of the material was placed in 10 ml distilled water vial and aliquots were sampled for dissolution as described above. See FIG. 18. Prolonged sustained release in a linear fashion was observed for about 272 days.

Figure 19:
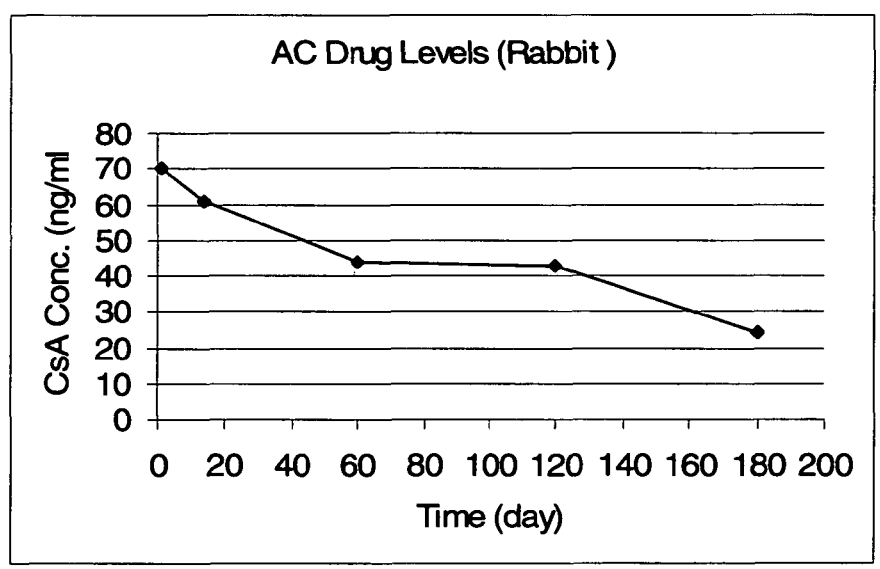
FIG. 19 depicts an in vivo release profile of cyclosporine from a tocopherol succinate:cyclosporin formulation implanted the anterior chamber of a NZW rabbit.
Figure 20:
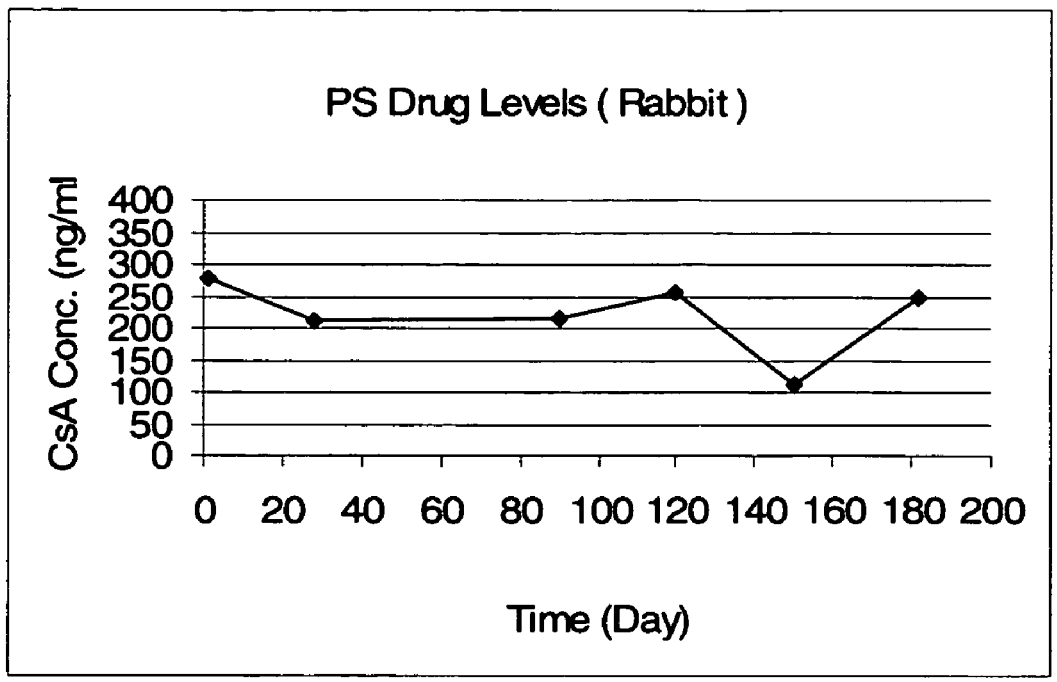
FIG. 20 depicts an in vivo release profile of cyclosporine from a tocopherol succinate:cyclosporin formulation implanted the posterior segment of a NZW rabbit eye.

To study the in vivo release profile, 0.75 mg of the 25:75 tocopherol succinate:cyclosporin was implanted surgically in the right anterior chamber (AC) of the 4.0 kg NZW female rabbit. The AC was tapped at the above time-points for HPLC determination of CsA in the aqueous humor. See FIG. 19. Additionally, 5.0 mg of 25:75 tocopherol succinate:cyclosporine was implanted surgically into the left posterior segment (PS) of a 4 kg NZW female rabbit eye. The vitreous humor in the PS was tapped at the above time-point for CsA HPLC analysis. See FIG. 20.

Figure 21:
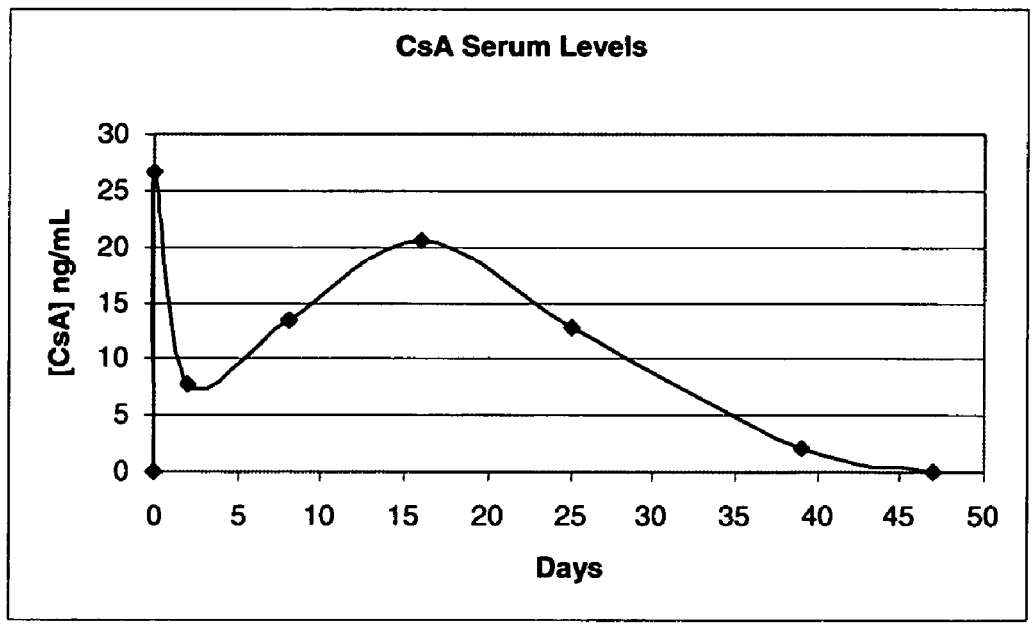
FIG. 21 shows an in vivo release of cyclosporine from a tocopherol succinate:cyclosporin formulation implanted in the peritoneal cavity of a rat.

In another in vivo release study, 30 mg (3×10 mg) of a 25:75 tocopherol succinate:cyclosporin formulation was extruded through a 1 mm aperature. The segments were implanted in the peritoneal cavity of an adult male Sprague-Dawley rat with a trocar through a 3 mm incision after local 0.5% lidocaine infiltration. Cardiac puncture was performed for blood CsA LCMSMS analysis. See FIG. 21.

Implants of cyclosporin:tocopherol succinate were injected by needle trocar in various organs in Sprague-Dawley rats to determine cyclosporin distribution. More specifically, extruded 20:80 tocopherol succinate:cyclosporin of various weights were implanted. After sacrifice and harvest, all tissues were dried in a tissue concentrator for 48 hours, crushed and soaked in 1 ml of MeOH containing 10 ng/ml CsD. Analysis were performed with Mass Spec Liquid Chromatography. CsA was observed as indicated below in Table 4 and Table 5. Abbreviations: ant anterior, post posterior, hem hemisphere.

TABLE 4

Cyclosporin distribution in rat liver and brain.

| | mg dried tissue | ng/ml CsA | ng/mg CsA |
|---|---|---|---|
| Liver #1 Upper Lobe, Sacrificed Day 5, 2 mg 80% CsA in tocopherol succinate was implanted into the right third of the middle lobe* | | | |
| Upper lobe | | | |
| right third | 71.4. mg | 2540 | 35.6 |
| middle third | 119.4 | 191 | 1.6 |
| left third | 88.4 | 184 | 2.1 |
| middle lobe | | | |
| right third* | 83.3 | 2360 | 28.3 |
| left third | 88 | 878 | 10 |

TABLE 4-continued

Cyclosporin distribution in rat liver and brain.

|  | mg dried tissue | ng/ml CsA | ng/mg CsA |
|---|---|---|---|
| left third | 49.2 | 2620 | 53.2 |
| blood | na | 0 | na |

Observation: CsA distribution was detected in both upper and middle lobes when implant was implanted in the middle lobe.*
Liver #2 Lower Lobe, Sacrifice 24 hours, 2 mg of implant injected.

| right fifth | 99.3 | 254 | 2.6 |
| right middle fifth | 59.6 | 144 | 2.4 |
| Implant* |  | 138.8 | 2420 |
| left middle fifth | 77.5 | 1710 | 22 |
| left fifth | 53.5 | 278 | 5.2 |

Observation: Sacrifice at 24 hours showed much higher concentration in the section of the liver containing the implant.
Brain #1, Sacrifice 24 hours, 1 mg of the formulation was implanted.

| left ant hem | 47.2 | 72.1 | 15.3 |
| left post hem | 79.3 | 180 | 2.3 |
| right ant hem* | 52.7 | 1190 | 22.6 |
| right post hem | 60.8 | 385 | 6.3 |
| blood | na | 0 | na |

Observation: CsA distribution was noted in both hemispheres even though the implant was placed in the right ant hem.*
Brain #2, 1 mg formulation implanted in right ant hem.*

| left ant hem | 42.2 | 478 | 11.3 |
| left post hem | 68.6 | 127 | 1.9 |
| right ant hem* | 73.9 | 401 | 5.4 |
| right post hem | 113.7 | 96 | 0.8 |
| blood | na | 0.29 | na |

Observation: Similar to brain # 1, the left ant hem showed much higher concentration.

*Site of implantation.

TABLE 5

Cyclosporin distribution in rat spleen and kidney.

|  | mg dried tissue | ng/ml CsA | ng/mg CsA |
|---|---|---|---|

Spleen, sections right to left, 1 mg implant in section #7.*

| section #1 | 10.3 | 217 | 21.1 |
| section #2 | 16.2 | 72.5 | 4.5 |
| section #3 | 12.9 | 17.7 | 1.4 |
| section #4 | 24.9 | 62 | 2.5 |
| section #5 | 22.5 | 72.9 | 3.2 |
| section #6 | 26.8 | 101 | 3.8 |
| section #7* | 29 | 1800 | 62 |
| blood | na | 0 | na |

Observation: Distribution appears higher at the opposite pole of the spleen.
Kidney, 075 mg implant in lower third.

| upper third | 156.8 | 314 | 2 |
| middle | 85.5 | 333 | 3.9 |
| lower third* | 106.1 | 165 | 1.6 |

Observation: CsA distribution throughout kidney.

*site of implantation.

Example 23

Transdermal Delivery of Insulin

The comparinson of injected versus transdermal delivery of several formulation of insulin was studied in a mouse model. One mg of porcine insulin was injected IP (intraperitoneal) into a mouse. A precipitous drop in glucose level was found within one-half hour and developed into hypoglycemia after one hour. Hypoglycemia persisted below perceptible levels and the animals never recovered. One mg of porcine insulin was mixed with 0.1 ml of tocopherol acetate and injected IP, perceptible drop in glucose level was seen up to 3 hours and the animal remained hypoglycemic and did not recover. IP glucose infusion did not reverse the hypoglycemia. One mg of porcine insulin mixed with 0.1 ml of tocopherol acetate was applied topically on the skin of a shaved mouse. Slow decline of glucose level was seen with the lowest level determined at 5.5 hours. Return towards pre-treatment levels was seen at 24 hour and 48 hour. Tocopherol IP was able to slow the hypoglycemic effect of insulin. Transdermal insulin w Topcopherol Ac produced reduction in glucose levels with slow recovery to pre-treatment levels after 24-48 hours. Sustained release of transdermal administered insulin was observed (data not shown).

Figure 22:
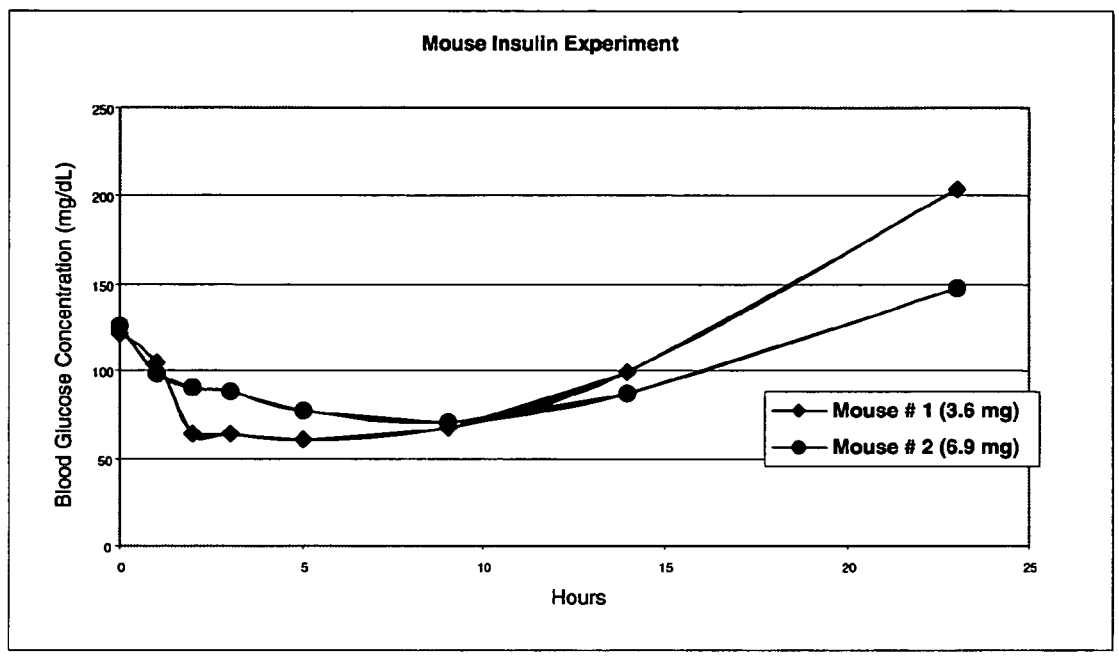
FIG. 22 plots in vivo blood glucose levels in mice treated with a transdermal formulation of insulin in tocopheryl acetate.

Porcine insulin (20 mg) was mixed in 199 mg/ml of tocopheryl acetate and formed a paste (or gel) which and was applied to the backs of shaved albino mice as follows. Mouse #1 was treated with 39.8 mg of insulin/tocopherol acetate paste, equaling 3.6 mg of insulin; mouse #2 was treated with 75.2 mg of insulin/tocopherol acetate paste, equaling 6.9 mg of insulin. Tail blood glucose levels were determined by Home Diagnostics, Inc. True Track smart system at intervals depicted in FIG. 22. A drop in glucose level was seen as early as one-half hour after transdermal application followed by sustained depressed levels for up to fifteen hours. By twenty-four hours, glucose had returned to pre-treatment levels followed by rebound ro hyperglycemic concentrations for the next twenty-four hours. Sustained release of transdermal administered insulin has been demonstrated.

Pharmaceutical agents that may be delivered by this platform include analgesics, anesthetics, narcotics, angiostatic steroids, anti-inflammatory steroids, angiogenesis inhibitors, nonsteroidal anti-inflammatories, anti-infective agents, anti-fungals, anti-malarials, anti-tuberculosis agents, anti-virals, alpha androgenergic agonists, beta adrenergic blocking agents, carbonic anhydrase inhibitors, mast cell stabilizers, miotics, prostaglandins, antihistamines, antimicrotubule agents, antineoplastic agents, antiapoptotics, aldose reductase inhibitors, antihypertensives, antioxidants, growth hormone antagonists, vitrectomy agents adenosine receptor antagonists, adenosine delaminate inhibitor, glycosylation antagonists, anti-aging peptides, topoisemerase inhibitors, anti-metabolites, alkylating agents, antiandrigens, anti-oestogens, oncogene activation inhibitors, telomerase inhibitors, antibodies or portions thereof, antisense oligonucleotides, fusion proteins, luteinizing hormone releasing hormones agonists, gonadotropin releasing hormone agonists, tyrosine kinase inhibitors, epidermal growth factor inhibitors, ribo-nucleotide reductase inhibitors, cytotoxins, IL2 therapeutics, neurotensin antagonists, peripheral sigma ligands, endothelin ETA/receptor antagonists, antihyperglycemics, anti-glaucoma agents, anti-chromatin modifying enzymes, obesity management agents, anemia therapeutics, emesis therapeutics, neutropaenia therapeutics, tumor-induced hypercalcaemia therapeutics, blood anticoagulants, anti-proliferatives, immunosuppressive agents, tissue repair agents, and psychotherapeutic agents. Aptamer (Eyetech), and Lucentis (Genentech) and RNA inhibitors., insulin, human insulin, GLP-1, Byetta (exenatide, Amylin).

Modifications of the above described modes for carrying out the invention that are obvious to those of ordinary skill in the surgical, pharmaceutical, or related arts are intended to be within the scope of the appended claims.

What is claimed is:

1. A pharmaceutical composition formulated for intraocular injection for the sustained release of an active agent comprising:
   at least one excipient selected from the group consisting of benzyl benzoate, ethyl benzoate, n-propyl benzoate, isopropyl benzoate, n-butyl benzoate and isobutyl benzoate;
   wherein the amount of the excipient is sufficient to dissolve, disperse, emulsify, or suspend the entire amount of the active agent in the composition, and wherein the concentration of excipient in the composition is higher than the concentration of any other constituent in the composition;
   wherein the composition releases the active agent for a period of at least about 60 days; and
   wherein the composition is a unit dosage formulation of about 5 μl to about 100 μl that can be injected through a 20 gauge or smaller size syringe needle into the subconjunctiva, periocular space, retrobulbar in the orbit, episclera, intracomea, intrasclera, anterior chamber, anterior segment, posterior chamber, posterior segment, vitreous cavity, subretinal space, suprachorodial segment or intraretinal area of the eye,
   such that upon initial injection said pharmaceutical composition maintains its monolithic integrity.

2. The composition of claim 1, wherein the active agent is an anti-inflammatory agent or an anti-angiogenesis agent.

3. The composition of claim 1, wherein the active agent is an anti-inflammatory agent selected from the group consisting of selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

4. The pharmaceutical composition of claim 1, wherein the excipient is benzyl benzoate and the active agent is selected from dexamethasone, dexamethasone analogs, dexamethasone derivatives, triamcinolone, triamcinolone analogs, and triamcinolone derivatives.

5. A prefilled container comprising the pharmaceutical composition of any one of claim 1, 2, 3, or 4.

6. A method of treating a malady of the eye comprising administering the pharmaceutical composition of claim 1 to a subject in need thereof, wherein said malady is selected from the group consisting of allergic and infectious conjunctivitis, uveitis of the anterior and posterior segments, infectious endophthalmitis of the anterior segment and posterior segment, dry-eye syndrome, post-surgical inflammation and infection of the anterior and posterior segments, angle-closure glaucoma, open-angle glaucoma, post-surgical glaucoma, exophthalmos, scleritis, episcleritis, Grave's disease, pseudotumor of the orbit, lymphoma of the orbit, tumors of the orbit, orbital cellulitis, blepharitis, intraocular tumors, retinoblastoma, malignant melanoma, retinal fibrosis, vitreous substitute and vitreous replacement, iris neovascularization from cataract surgery, macular edema in central retinal vein occlusion, cellular transplantation, cystoid macular edema, pseudophakic cystoid macular edema, diabetic macular edema, diffuse diabetic macular edema, pre-phthisical ocular hypotomy, proliferative vitreoretinopathy, proliferative diabetic retinopathy, macular degeneration, extensive exudative retinal detachment, diabetic retinal edema, retinitis pigmentosa, ischemic ophthalmopathy, chronic focal immunalogic and chemical corneal graft reaction, neovascular glaucoma, pars plana vitrectomy, sympathetic ophthalmia, intermediate uveitis, chronic uveitis, intraocular infection, endophthalmitis, Irvine-Gass syndrome, conditions of inflammatory and immunological nature, sequelae of surgical complications, acquired and hereditary ocular conditions, Tay-Sach's disease, Niemann-Pick's disease, cystinosis, corneal dystrophies, and multiple myeloma.

7. The method of claim 6, further comprising repeating said administering after at least 4 months.

8. A method for treating inflammation or angiogenesis of the eye in an individual comprising: injecting into the vitreous of the eye a formulation consisting of
   at least one anti-angiogenesis agent or anti-inflammatory agent; and
   at least one biocompatible, biodegradable excipient selected from the group consisting of benzyl benzoate, ethyl benzoate, n-propyl benzoate, isopropyl benzoate, n-butyl benzoate, and isobutyl benzoate;
   wherein the formulation releases into the vitreous a therapeutic dose of the anti-angiogenesis agent or anti-inflammatory agent for at least two months.

9. The method of claim 8, further comprising repeating said injecting after at least four months.

* * * * *